United States Patent
Bentz

(10) Patent No.: US 10,266,329 B2
(45) Date of Patent: Apr. 23, 2019

(54) PACKAGES AND METHODS FOR MANUFACTURING PACKAGES

(71) Applicant: Bemis Company, Inc., Neenah, WI (US)

(72) Inventor: Aaron R. Bentz, Neenah, WI (US)

(73) Assignee: Bemis Company, Inc., Neenah, WI (US)

(*) Notice: Subject to any disclaimer, the term of this patent is extended or adjusted under 35 U.S.C. 154(b) by 53 days.

(21) Appl. No.: 15/175,908

(22) Filed: Jun. 7, 2016

(65) Prior Publication Data

US 2017/0349347 A1     Dec. 7, 2017

(51) Int. Cl.

| | | |
|---|---|---|
| *B65D 75/30* | (2006.01) | |
| *B65D 65/14* | (2006.01) | |
| *B32B 27/06* | (2006.01) | |
| *B32B 7/12* | (2006.01) | |
| *B65D 75/58* | (2006.01) | |
| *B32B 7/06* | (2019.01) | |
| *B32B 3/26* | (2006.01) | |
| *A61B 50/30* | (2016.01) | |
| *A61B 50/00* | (2016.01) | |

(52) U.S. Cl.
CPC .......... *B65D 75/5827* (2013.01); *A61B 50/30* (2016.02); *B32B 3/266* (2013.01); *B32B 7/06* (2013.01); *B32B 7/12* (2013.01); *B32B 27/06* (2013.01); *B65D 65/14* (2013.01); *B65D 75/30* (2013.01); *A61B 2050/006* (2016.02); *A61B 2050/314* (2016.02); *B32B 2439/00* (2013.01); *B32B 2439/80* (2013.01)

(58) Field of Classification Search
CPC .... B65D 75/5827; B65D 75/30; B65D 75/66; B65D 75/68; B65D 33/2533; B65D 33/2583; B65D 77/32; B65D 65/14; B32B 3/266; B32B 7/06; B32B 7/12
USPC ...... 229/87.1; 388/207, 209, 208; 206/484.2
See application file for complete search history.

(56) References Cited

U.S. PATENT DOCUMENTS

| | | |
|---|---|---|
| 3,372,799 A | 3/1968 | Abildgaard et al. |
| 3,405,563 A | 10/1968 | Kugler et al. |
| 3,437,258 A | 4/1969 | Kugler et al. |
| 4,116,338 A | 9/1978 | Weichselbaum |
| 4,294,360 A | 10/1981 | LeVeen |
| 4,904,093 A | 2/1990 | Woods et al. |
| 5,638,661 A | 6/1997 | Banks |
| 5,704,670 A | 1/1998 | Surplus |
| 5,816,403 A | 10/1998 | Wilkes et al. |
| 6,203,080 B1 | 3/2001 | Surplus |

(Continued)

FOREIGN PATENT DOCUMENTS

| | | |
|---|---|---|
| WO | WO2015002651 | 1/2015 |
| WO | WO2015112110 | 7/2015 |
| WO | 2015139941 A1 | 9/2015 |

OTHER PUBLICATIONS

U.S. Appl. No. 14/986,438, Aaron R. Bentz.

*Primary Examiner* — Chun Hoi Cheung
(74) *Attorney, Agent, or Firm* — Lynn M. Nett

(57) ABSTRACT

A package that includes a housing portion, a handling portion and a separation feature. The separation feature facilitates separation of the handling and housing portions. The separation feature includes a first release layer and a second release layer adjacent to the first release layer provided between the first and second films at an overlapping portion of the housing portion and the handling portion.

6 Claims, 13 Drawing Sheets

(56) References Cited

U.S. PATENT DOCUMENTS

| | | | |
|---|---|---|---|
| 6,383,592 B1 * | 5/2002 | Lowry | B65D 31/02 |
| | | | 206/459.5 |
| 6,578,348 B1 | 6/2003 | Banks | |
| 6,672,036 B2 | 1/2004 | Banks | |
| 7,717,620 B2 * | 5/2010 | Hebert | B29C 59/007 |
| | | | 383/116 |
| 7,718,433 B2 | 5/2010 | Stecklein et al. | |
| 7,938,580 B2 | 5/2011 | Gaskell et al. | |
| 8,245,487 B2 | 8/2012 | Gammons | |
| 8,475,365 B2 | 7/2013 | Modin et al. | |
| 9,468,584 B2 * | 10/2016 | Riis | B65D 65/40 |
| 9,902,541 B2 * | 2/2018 | Cheema | B65D 65/22 |
| 2005/0112758 A1 | 5/2005 | Archambault et al. | |
| 2013/0224346 A1 * | 8/2013 | Cheema | B65D 65/22 |
| | | | 426/122 |
| 2014/0072247 A1 | 3/2014 | McDonough | |
| 2015/0283029 A1 * | 10/2015 | Riis | B65D 65/40 |
| | | | 206/438 |

* cited by examiner

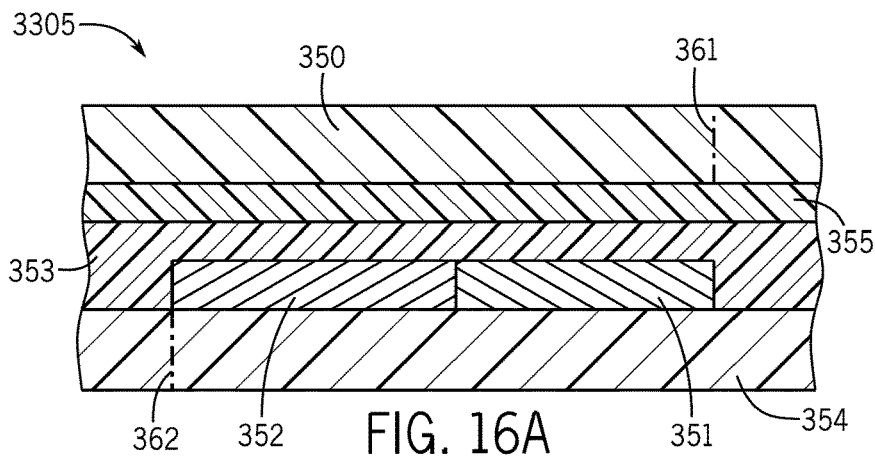
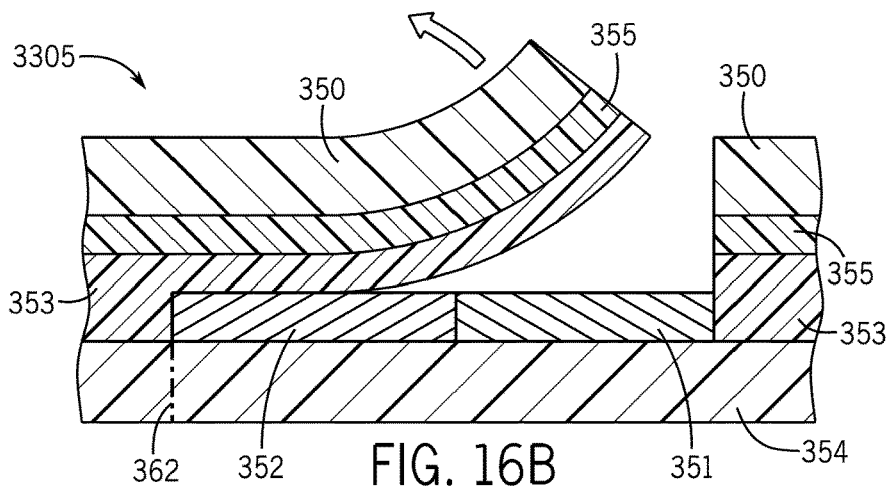
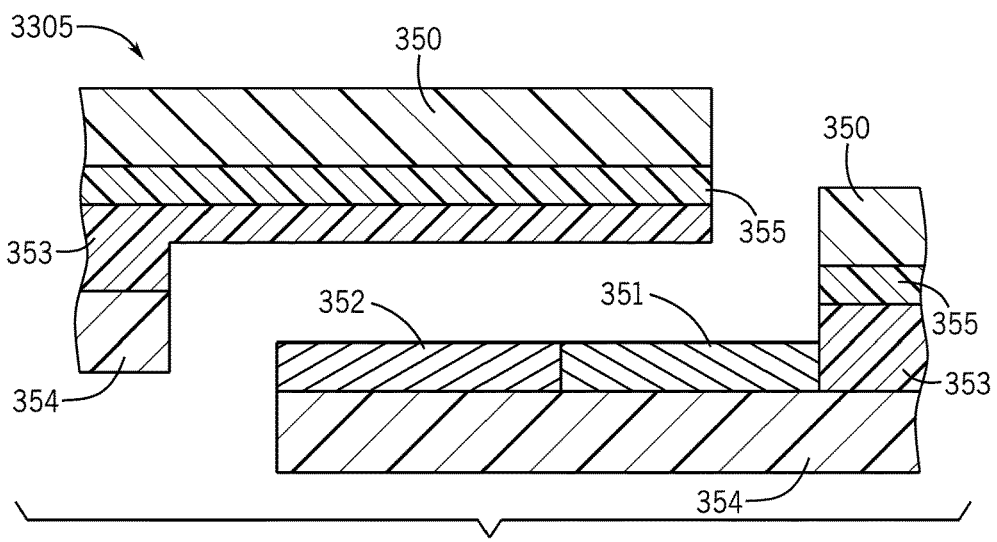

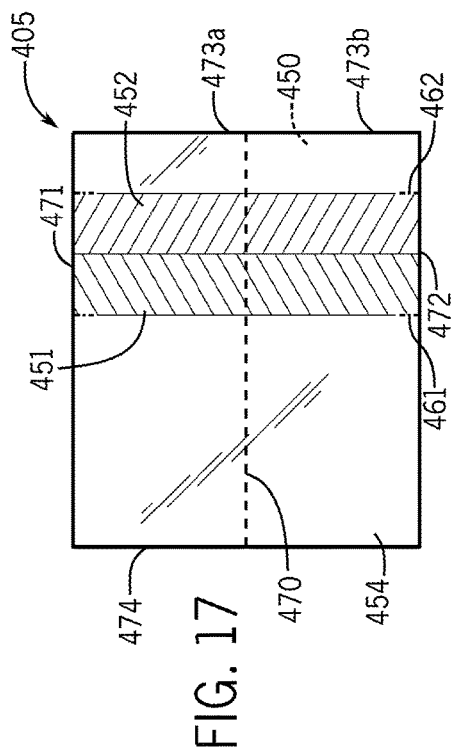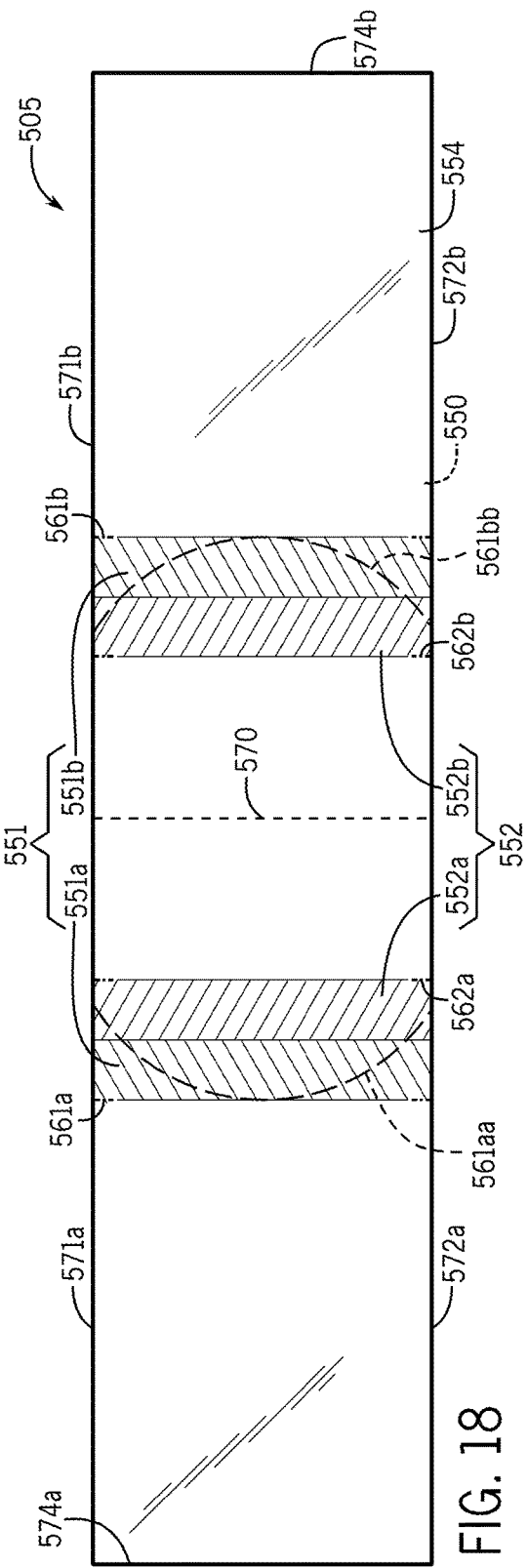

PACKAGES AND METHODS FOR MANUFACTURING PACKAGES

BACKGROUND

The present application relates generally to the field of packages for containing a product and methods for the manufacture of such packages. More specifically, this application relates to packages having a housing portion configured to contain a product and a handling portion that is separable from the housing portion and can be used to handle the product.

Packages are used to contain products in a generally enclosed space (e.g., environment), such as for transporting the products, protecting the products, or for other useful purposes. In certain applications, such as, for example medical related applications, it is necessary to maintain a sterile environment for the product so as to allow for a sterile presentation of the product (e.g., in the case of a medical device or product, to allow for the product to be easily removed from the package without compromising the sterile nature of the product). In certain applications, it is necessary to maintain aseptic environments to allow for aseptic presentation of the product contained in the package. For these applications, exposure to non-sterile/septic conditions/surfaces (e.g., the exterior of the package or something exterior to the package itself that can come into contact with the product, such as a hand of a medical professional) must be avoided to avoid contamination of the product and maintain the sterile presentation.

Thus, it is desirable to provide packages having an improved construction that allows for separation of the package into two portions. For example, the packages can be separated to provide an improved sterile presentation, such as by mitigating the risk of contamination of a contained product to maintain a sterile presentation. It is also desirable to provide packages that simplify the process of removing the product therefrom with a minimum number of hands/steps.

SUMMARY

One embodiment relates to a package that is configured to contain and provide for sterile presentation of a product. The package includes a housing portion, a handling portion, and a separation feature. The housing portion defines an interior product storage cavity and includes a first part of a first film, a first part of a second film, and a first part of a bonding layer coupling the first part of the first film to the first part of the second film. The handling portion is configured to extend away from the storage cavity of the housing portion. The handling portion includes a second part of the first film, a second part of the second film, and a second part of the bonding layer coupling the second part of the first film to the second part of the second film. The separation feature is configured to facilitate separation of the handling portion and the housing portion. The separation feature includes a first release layer and a second release layer adjacent to the first release layer provided between the first film and the second film at an overlapping portion of the housing portion and the handling portion.

Another embodiment relates to a flexible multilayer film for use in forming a package configured to contain and provide for sterile presentation of a product. The multilayer film includes a first film having a surface, a first release layer on a first portion of the surface of the first film, second release layer adjacent to the first release layer on a second portion of the surface of the first film, a second film located to a side of the first release layer and the second release layer that is opposite a side of the first release layer and a second release layer in contact with the surface of the first film, and a bonding layer coupling the first film to the second film, the first release layer, and the second release layer. The bond strength of the second release layer to the bonding layer is less than the bond strength of the first release layer to the bonding layer.

Yet another embodiment relates to a method of manufacturing a flexible multilayer film for use in forming a package configured to contain and provide for sterile presentation of a product. The method includes providing a first film having a surface, providing a second film having a surface, disposing a first release layer on a first portion of the surface of the first film, and disposing a second release layer adjacent to the first release layer on a second portion of the surface of the first film. The method also includes disposing a bonding layer on the first release layer, the second release layer, and at least a third portion of the surface of the first film. The method also includes coupling the second film to the adhesive layer at a side of the adhesive layer distal to the first release layer and the second release layer.

BRIEF DESCRIPTION OF THE DRAWINGS

FIG. 16A is a cross-sectional view taken along line 9-9 of FIG. 3 illustrating an eighth embodiment.

FIG. 16B is the cross-sectional view of the eighth embodiment shown in FIG. 16A during separation.

FIG. 16C is the cross-sectional view of the eighth embodiment shown in FIG. 16A after separation.

FIG. 17 is a plan view of an exemplary embodiment of a film shown in the flat prior to forming a package.

FIG. 18 is a plan view of another exemplary embodiment of a film shown in the flat prior to forming a package.

DETAILED DESCRIPTION

Referring generally to the FIGURES, disclosed in this application are packages (e.g., packaging, pouches, etc.), films (e.g., multilayer films) for such packages, and methods of manufacturing (e.g., making, forming, assembling, etc.) such packages. The packages include a housing portion (e.g., sleeve, retainer, retaining portion, etc.) and a handling portion (e.g., gusset, grabbing portion, glove, etc.), which together form a structure (e.g., container, storage receptacle, etc.) that can be configured to be airtight (e.g., form a hermetic seal). The housing portion is configured to contain (e.g., hold, retain, house, seal, enclose, etc.) a component (e.g., element, product, device, product, etc.). The handling portion may be inwardly facing or adjustable (e.g., positionable, etc.) to be inwardly facing and can be used to grip the component contained within the housing portion. The housing portion and handling portion may be configured to be separable, so as to allow for the removal of the component from the package.

The packages also include a separation feature configured to facilitate separation of the housing and handling portions. The separation feature includes two or more release layers with a gradient of bond strengths (e.g., different bond strengths). The separation feature may include one or more (e.g., two, four, etc.) features (e.g., lines of weakness, nicks, recesses, perforations, abrasions, areas or regions having differing material properties or orientations, etc., generally referred to herein as "weakening features") that are configured to facilitate separation between the housing portion and the handling portion. For example, the weakening feature may include two lines of weakness, with each line of weakness extending through one or more layers of the package.

According to an exemplary embodiment, the packages disclosed in this application are configured to allow for sterile presentation of a component contained therein, such as, for example, by providing a hermetic seal around a medical device to be presented by a medical professional to a surgeon during an operation. Advantageously, the packages disclosed herein may allow for sterile presentation of the component (e.g., by maintaining the component in an airtight sterilized enclosure) without the need to slide the component onto a surface (which may not be sterile) or to reach in and remove the component out of the package without touching the sides of the package. According to an exemplary embodiment, the handling portion allows for the component to be gripped with a first hand while the housing portion and handling portion are separated with a second hand (of the same person as the first hand or an additional person). The housing portion can then be removed with the second hand while continuing to grip the component (or a tray or other structure in which the component is located) in the first hand.

Figure 1:
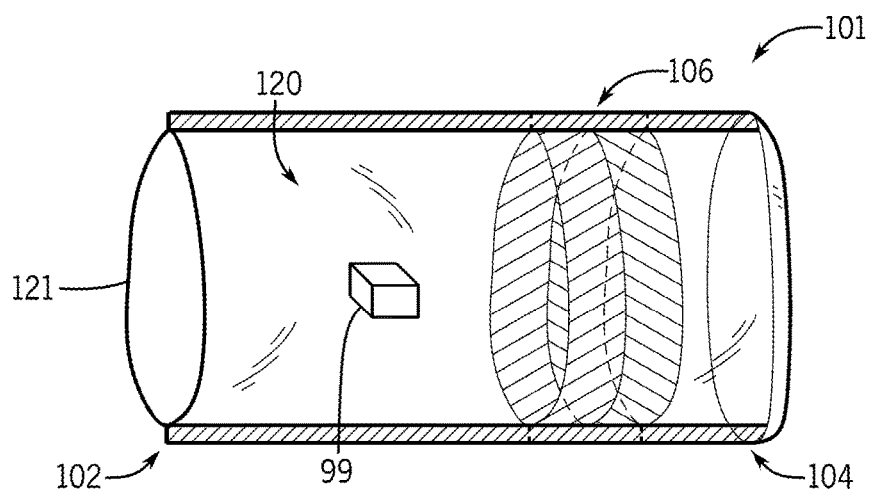
FIG. 1 is a perspective view of a package for containing a product according to an exemplary embodiment.
Figure 2:
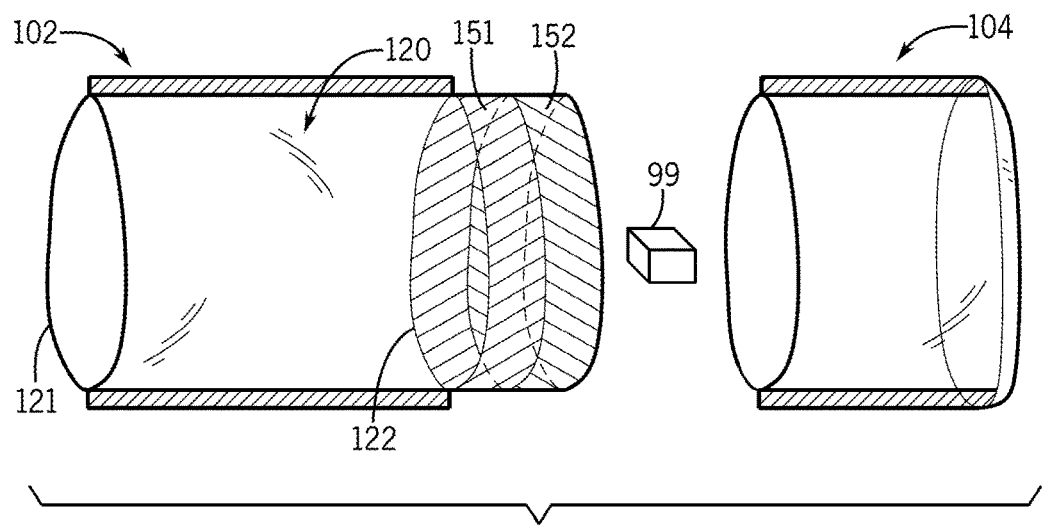
FIG. 2 is a partially exploded perspective view of the package of FIG. 1 shown before sealing a product into the package.

Now referring specifically to the accompanying drawings, FIGS. 1 and 2 illustrate an exemplary embodiment of a package 101 that is configured to contain a product 99 (e.g., a component, device, element, object, etc. shown generally in the form of a cube but being understood to have any of a wide variety of shapes, sizes, and/or configurations) therein. According to an exemplary embodiment, the package 101 is configured to contain the product 99, such as a medical device, in an interior cavity 120 within the package 101 that is a sterile environment to help provide for a sterile presentation of the product. The product may include one element (e.g., a medical device, a medical instrument, etc.) or may include more than one element, such as, for example, a medical device inside of a carrier such as a tray or other structure. As non-limiting examples, the medical devices/instruments can be implantable devices (e.g., hip implants, stents, etc.), instruments (e.g., scalpels, scissors, syringes, sponges, etc.), or any other device/product that could benefit from being maintained in a sterile environment. Other sterile applications can involve pharmaceutical products, biotechnology products, food products, as well as any other product that would benefit from a sterile environment.

Other types of products can be contained in the packages disclosed herein according to other exemplary embodiments. For example, rather than maintaining a sterile presentation, the packages of this application could be configured to insulate (e.g., thermally, electrically, etc.) a user from the product contained in the package, such as by configuring the package to be insulating. Also for example, the packages disclosed herein may be configured to contain electronic components, mechanical components, specially coated surfaces, chemicals, microbiological materials, food products, halogen lamps or other products that may be detrimentally affected by interaction with human skin/oils, products including components toxic to humans, or any other types of products. The packages can provide anti-static or static-resistant enclosures for electronic components. As still another example, the packages can house mechanical components that are greasy (e.g., oily, lubricated, etc.) in an effort to prevent the spread of oil/lubricant to other elements or to maintain the necessary lubrication of the components prior to assembly or use.

Figure 6:
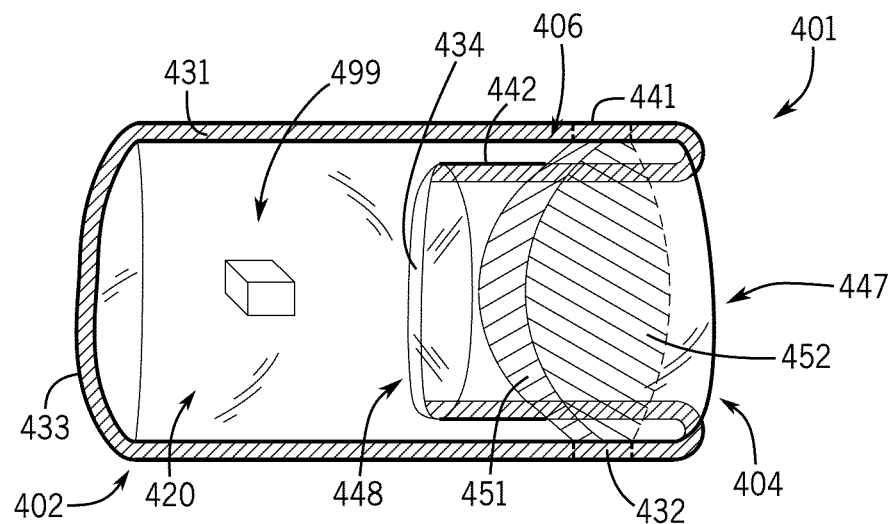
FIG. 6 is a perspective view of a package for containing a product according to another exemplary embodiment.

As shown in FIG. 1, the product 99 can be placed (e.g., assembled, inserted, implanted, etc.) into the package 101 after assembly of the package 101, such as through the open first end 121 by a customer or other party. The open first end 121 may then be sealed to contain the product 99 in the package 101. By way of example, FIG. 6 shows the third side 433 (which corresponds to the open end 121 of the package 101 after sealing) sealed/closed with the product 499 in the package 401. The packages that, for example, are intended to help provide for a sterile presentation of the product can be sealed in a manner that is substantially impervious to air, bacteria, and other elements that would negatively impact the sterile environment. Typically, the sterilization process would be performed after the product is placed in the package.

Figure 3:
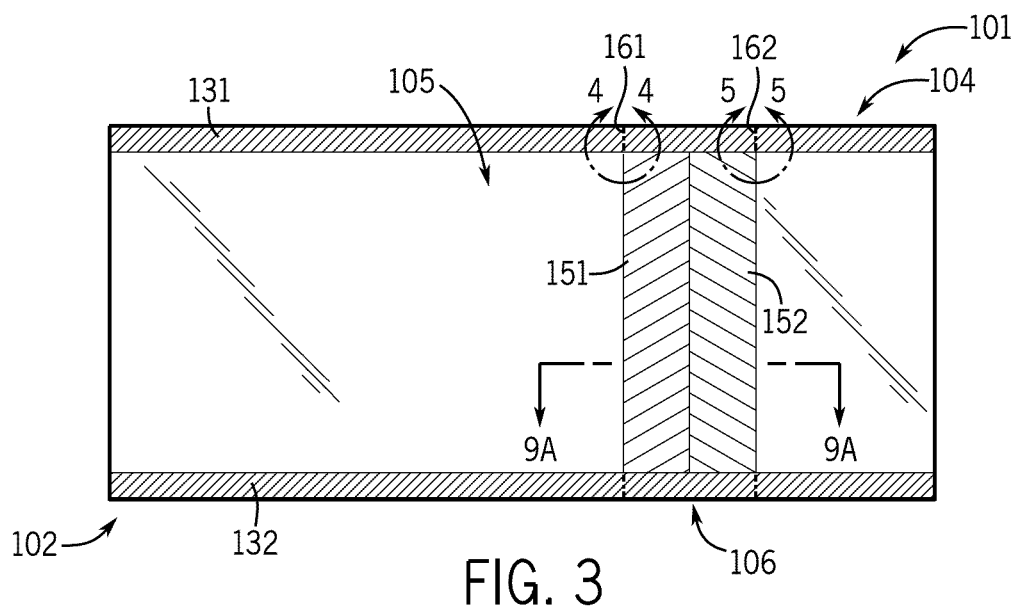
FIG. 3 is a side view of the package shown in FIG. 1, without the product.

Also shown in FIGS. 1 and 2, the package 101 includes a housing portion 102, a handling portion 104, and a separation feature 106. Together, the housing portion 102 and the handling portion 104 are configured to form a package (e.g., pouch, bag, etc.), such as, for example, a structure of the package, that can contain the product 99 therein. As shown in FIG. 3, the package 101 includes a first sealed side 131 and a second sealed side 132. A third side (e.g., the right side shown in FIG. 3) may be a fold side that forms a sealed side, such as discussed in more detail below.

Figure 4:
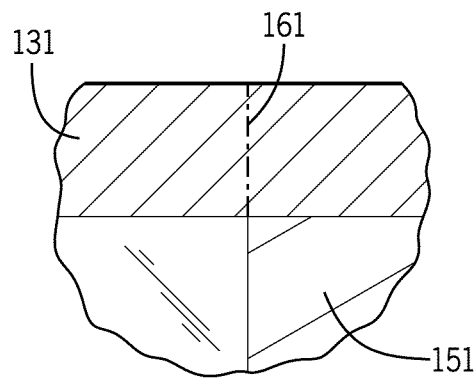
FIG. 4 is a detail view of a portion of the package shown in FIG. 3.
Figure 5:
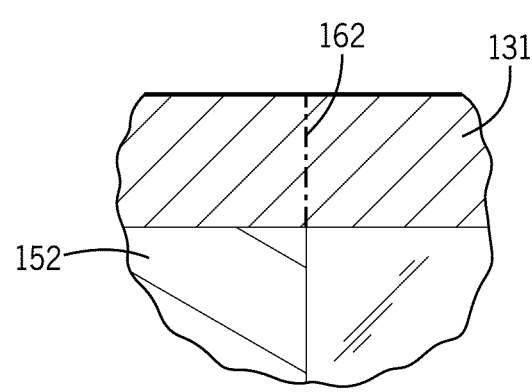
FIG. 5 is another detail view of a portion of a package shown in FIG. 3.

The separation feature 106 of the package 101 is configured to facilitate separation (e.g., detaching, removing, etc.) of the handling portion 104 and the housing portion 102, so as to allow access to the product stored in the package (e.g., the housing portion 102). As shown best in FIGS. 3-5, the separation feature 106 includes a first release layer 151, a second release layer 152 adjacent (e.g., juxtaposed) to the first release layer 151, a first line of weakness 161 aligned with (e.g., overlapping, overlying) the first release layer 151, and a second line of weakness 162 aligned with (e.g., overlapping, overlying) the second release layer 152. For example, each line of weakness 161, 162 may be substantially aligned with an edge (e.g., outside edge) of the associated release layer 151, 152.

Figure 7:
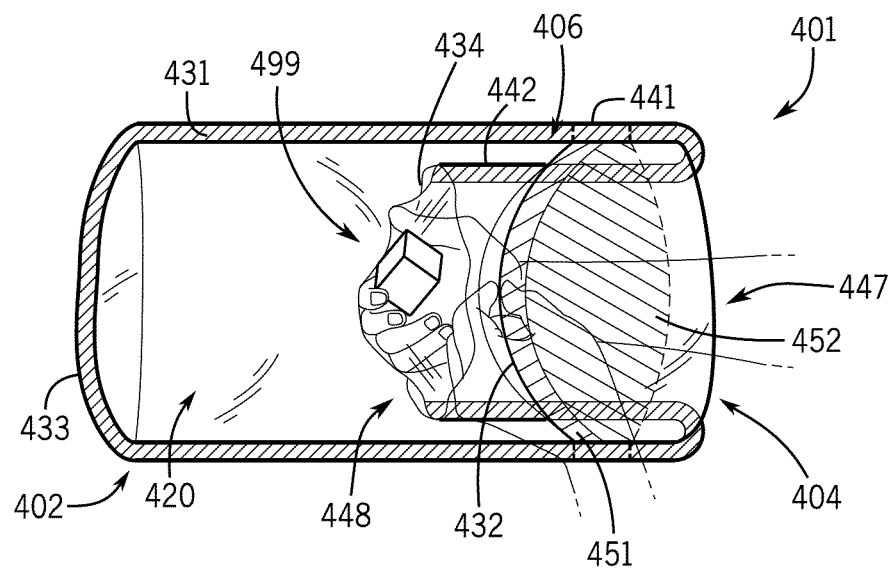
FIG. 7 is a perspective view of the package shown in FIG. 6 with a person grasping the product through the handling portion of the package with one hand and peeling the separation feature to separate the housing and handling portions of the package with the other hand.
Figure 8:
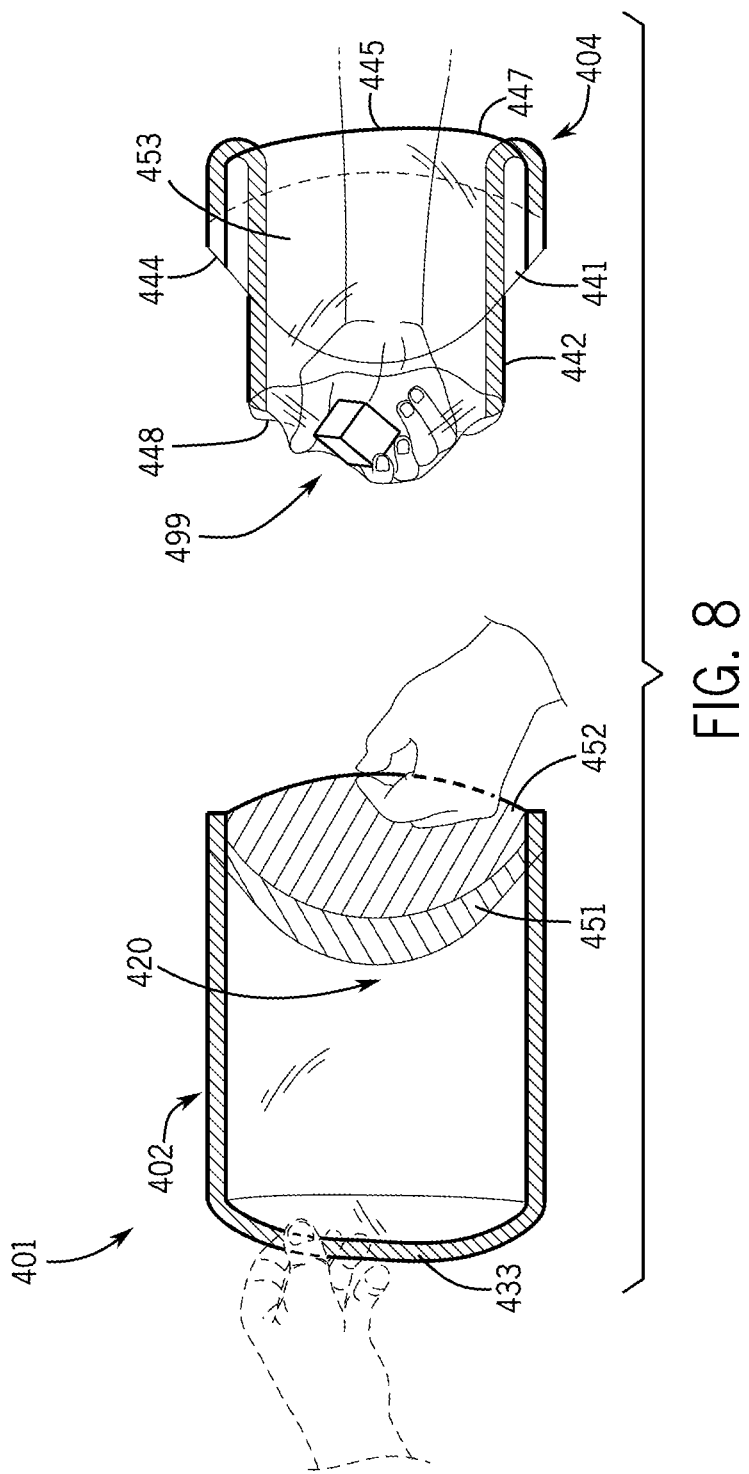
FIG. 8 is a perspective view of the package shown in FIG. 6 in a separated configuration that is intended to allow for removal of a product from the package with the person grasping the product through the handling portion of the package with the one hand and pulling the housing portion of the package away from the handling portion with the other hand.

As shown best in FIGS. 1 and 2, each first release layer 151, 152 may have a generally annular (e.g., ring, cylindrical, etc.) shape or another suitable shape (the term generally annular conveys that due to the flexible nature of the film and package, the shape of the layers may be manipulated into other shapes) that extends around (e.g., completely around, substantially around) at least a portion of the package. The size (e.g., width) of each release layer may remain generally constant around the entire package, such as shown in FIG. 3, or the size of one or both release layers may vary moving around the package. By way of example, the package 401 shown in FIGS. 6-8 illustrate release layers 451, 452 that change in width moving around the annular shaped package 401. The release layers and the lines of weakness are discussed in more detail below. Once separated, the handling portion 104 is configured to facilitate handling of the product. For the packages that help provide for a sterile presentation, the handling portion 104 is configured to act as a barrier between the hand(s) of a user (e.g., doctor, nurse, other suitable medical person or technician, etc.) and the sterile product (e.g., medical device, instrument, etc.) to maintain the sterile nature of the product prior to use (e.g., surgery, administration, etc.). It is noted that FIG. 1 shows the handling portion 104 and housing portion 102 prior to separation, and FIG. 2 shows the package partially exploded to illustrate the handling portion 104 separated from the housing portion 102.

The housing portion 102 is configured as a hollow member, shown generally tubular, that defines the interior cavity 120 for containing the product therein. As shown in FIGS. 1 and 2, the housing portion 102 of the package 101 is configured generally as a sleeve-shaped element that extends from a first end 121 to a second end 122. However, the housing portion 102 may be configured having other shapes (e.g., generally rectangular, generally cubic, etc.). Further, the housing portion 102 is made from a flexible film material, such as one of the flexible multilayer films disclosed herein, that allows the housing portion 102 to be reshaped (e.g., reconfigured, manipulated into other shapes, etc.).

The first end 121 of the housing portion 102 may be an open end (e.g., not sealed), so as to allow the product to be inserted into the cavity 120 through the open first end 121 after the package 101 is formed. The first end 121 may then be sealed using a heat seal or other suitable sealing process (the product may be inserted and the package sealed either by the package manufacturer or by a third party to which the package may be sent with the open first end 121).

The second end 122 of the housing portion 102 is initially coupled to the handling portion 104 and opening the package allows access to the product contained in the housing portion 102 (i.e., after the handling portion 104 and the housing portion 102 are separated). As shown in FIG. 2, after the handling portion 104 and the housing portion 102 are separated, the product 99 can be accessed and removed from the cavity 120 through the open second end 122 of the housing portion 102, such as using the handling portion 104.

The handling portion 104 together (e.g., in combination) with the housing portion 102 is configured to form a structure (e.g., a container) of the package 101. For example, the handling portion 104 may be integrally formed with the housing portion 102, such as from a single piece of material. For example, the handling portion 104 and the housing portion 102 may be integrally formed from a single piece of a film 105 (e.g., a panel, etc.), as shown in FIG. 3. As discussed in more detail below, the handling portion 104 and the housing portion 102 are configured to be separated from through a separation feature, such as, for example, the separation feature 106. Also discussed in more detail below, the handling portion 104 may be configured to help provide an aseptic/sterile presentation of the product 99 by allowing a user to handle the product using the handling portion 104.

As already noted, the package 101 (e.g., the housing portion 102, the handling portion 104, the separation feature 106, etc.) may include one or more than one piece of material, which may be formed into the desired shape. Each piece of material may include only a single layer structure or may include a multilayer configuration that is flexible enough to be manipulated into any desired shape (e.g., through forming, folding, etc.) and is capable of forming an air-tight seal, such as when sealed.

FIGS. 6-8 illustrate another exemplary embodiment of a package 401 that is configured to contain a product 499, such as in a sterilized environment (e.g., provide for sterile presentation). The package 401 is formed from a film, as disclosed herein, such as the film 405, 505 (e.g., see FIGS. 17 and 18). FIG. 6 shows the package 401 sealed on a first side 431, a second side 432, and a third side 433 using a sealing process. A fourth side 434 is formed with a fold line (e.g., the fold line 470 in FIG. 17). The product 499 is housed in an internal cavity 420 of the package 401 (e.g., in the housing portion 402).

FIGS. 7 and 8 show an exemplary method of removing the product 499 from the package 401. FIG. 7 illustrates a person grasping the product 499 through the handling portion 404 of the package 401 with one hand (e.g., the right hand) and peeling the separation feature to separate the housing portion 402 of the package 401 and the handling portion 404 with the other hand (e.g., the left hand). For clarity, the right hand is shown surrounded by a gripping portion of the handling portion of the package and the left hand is shown exterior to the package. For example, the film of the handling portion 404 can be peeled, such as starting from an apex of a curved portion of the film of the handling portion 404, from the film of the housing portion 402 to separate the two portions (e.g., the person moving his/her left hand, as shown, away from his/her body). Starting from an apex of a curved profile of the curved portion may advantageously be easier to peel, since, for example, there is relatively smaller area of film (e.g., of the handling portion 404) adhered at the apex compared to other regions of the film, such as near the base (e.g., the valley). Moreover, the apex provides a convenient point at which to grasp the film (e.g., effectively acting as a pull tab). That being said, peel initiation may be achieved at any point along a first line of weakness overlaying (e.g., overlapping) a first release layer.

FIG. 8 illustrates the package 401 in a separated configuration (e.g., with the housing portion 402 and the handling portion 404 fully separated from one another). Once a closed package has been transitioned to the separated configuration, the product 499 can be readily removed from the internal cavity 420 of the housing portion 402. A person grasping the product 499 with one hand (e.g., right hand, as shown) facilitates removal of the product 499 in a sterile manner, as discussed in more detail below.

Referring generally to FIG. 7 and FIG. 8, the package 401 includes a housing portion 402, a handling portion 404, and a separation feature 406. The housing portion 402 is configured substantially the same as the housing portion 102 of the package 101, except where noted otherwise. Therefore, further description of certain characteristics/features of the housing portion 402 is not required.

As shown, the handling portion 404 is configured substantially the same as the handling portion 104 of the package 101, except that the handling portion 404 is further manipulated (e.g., folded, formed, moved, etc.) to define a cuff 441 (e.g., cover, outer sleeve, etc.) and the gripping portion 442 (e.g., hand enclosure, glove, bag, extrusion, protrusion, etc.). The cuff 441 is configured to surround the separation feature 406 prior to separation of the handling portion 404 and the housing portion 402. Following separation of the handling and housing portions 404, 402, the sterile separation feature 406 reduces the risk of contamination of a sterile product (e.g., product 499) during removal of the product from the housing portion 402, since the separation feature 406 is located at the end of the housing portion from which the product is being withdrawn. Thus, the risk of contacting the sterile product with a contaminated part of the package (e.g., the outside of the housing portion 402) is greatly reduced.

As shown in FIG. 8 following separation of the handling portion 404 and the housing portion 402, the cuff 441 extends from a first cuff end 444 to a second cuff end 445. The first cuff end 444 of the cuff 441 may be configured to extend from the separation feature 406 and/or the housing portion 402, such as an end thereof. The first cuff end 444 of the cuff 441 may be defined by a line of weakness or may form as a result of separation along a section of the package 401 other than along a line of weakness. The second cuff end 445 of the cuff 441 may define an end of the package 401 when the gripping portion 442 is moved into the cuff 441 facing toward the product 499.

The cuff 441 of the handling portion transitions to the gripping portion 442. As shown in FIGS. 6-8, the gripping portion 442 is configured to extend inside (e.g., within, through, etc.) the cuff 441 and/or the separation feature 406 and toward the housing portion 402, such as toward the internal cavity 420 thereof and/or the closed third side 433 of the package 401.

The gripping portion 442 includes a first end 447 extending from the second cuff end 445 of the cuff 441 and a second end 448 that is provided within the housing portion 402 (prior to separation of the housing and handling portions, as shown in FIG. 6). The first end 447 of the gripping portion 442 is an open end to allow a user to place his/her hand into the gripping portion. The second end 448 of the gripping portion 442 is configured to allow a user to grasp (e.g., hold, grab, etc.) the product (housed in the housing portion). Thus, a person can place a hand/arm into the open first end 447 of the gripping portion 442 and grasp the product 499 using the closed second end 448 of the gripping portion 442 to help provide for a sterile presentation of the product 499 upon removal of/from the housing portion 402. As is evident from the above, the closed second end 448 is disposed between the person's hand and the product 499, providing a barrier. This advantageously allows for a sterile product housed in the package 401 to be grasped by a user with the internal/sterile side of the second end 448 of the gripping portion 442, avoiding the need for one to reach into the package (from the exterior) to access the product and present it in a sterile manner (e.g., the person operating the gripping portion may be able to directly place the product onto a sterile surface, such as, for example, sterile hands, sterile table, or any other sterile surface). Also shown in FIG. 8, while a person grasp's the product 499 with one hand (e.g., the right hand as shown), the person can peel and separate the portions (e.g., the housing portion 402 and the handling portion 404) with the person's other hand (e.g., the left hand shown in solid lines) in the same step making the process more effective. Of course, the person can hold the housing portion 402 in other locations when separating the portions, such as, for example, at the third side 433 (shown as the left side of the housing portion in FIG. 8) after peeling the film, as shown using the dashed left hand of the person in FIG. 8.

Also shown in FIGS. 6-8, the general shape of the first and second release layers 451, 452 are different than the release layers 151, 152 shown in FIGS. 1 and 2. As shown, the first release layer 451 has a first side (e.g., left side shown in FIG. 6) that has a generally circular (e.g., annular) shape and a second side (e.g., right side shown in FIG. 6) that has a generally arcuate shape (e.g., when viewed in pure side view). Also shown, the second release layer 452 has a first side (e.g., left side shown in FIG. 6) that has a generally arcuate shape, which matches the shape of the first release layer 451 since in this configuration the first side of the second release layer 452 abuts (e.g., contacts) the second side of the first release layer 451. The second release layer 452 also has a second side (e.g., right side shown in FIG. 6) that has a generally arcuate shape, such as when viewed in pure side view. The arcuate shape of the second side of the second release layer 452 may be the same arcuate shape as the first side or may be a different arcuate shape altogether. As noted above, the terms "generally annular" and "generally arcuate" are used to convey that the shapes may be changed by manipulation due to the flexible nature of the film and package. The arcuate shape may advantageously make it easier to initiate separation of the housing portion 402 from the handling portion 404) by peeling up an edge (defined by at least one of the lines of weakness, which are discussed elsewhere). More generally, any shape that makes it easier to initiate peel and/or establish a good point at which to hold the package (e.g., a peel tab, etc.) while initiating separation of the package is desirable, though not required. For example, shapes having a taper (either linearly or in a curved manner) may work well for one or more release layers because they may help provide a logical point for peel initiation and help provide a smooth separation when the pull force is applied. Symmetrical shapes with a taper can be particularly beneficial for a smooth separation, but are not required. Notably, the shapes of the release layers in the various embodiments disclosed in this application may have other suitable shapes and the shapes disclosed herein are exemplary and not limiting.

According to yet other examples, the gripping portion 442 of the handling portion 404 may be further manipulated, such as, for example, to form a "W" shape at the closed second end 448. The end formed by the fold line (e.g., fold line 470 shown in FIG. 17) can be manipulated (e.g., moved, pushed, etc.) back into the handling portion 404 toward the open first end 447 (through which a person can insert their arm) to form the inverted "V" shaped portion of the "W" shape. A person can place their hand into the gripping portion 442, such that the apex of the inverted "V" shaped portion points toward (or rests in) the palm of their hand with their fingers extending between one wall defining the inverted "V" shape and the outer wall of the handling portion forming the "W" shape, and with their thumb extending between the other wall defining the inverted "V" shape and the other outer wall of the handling portion forming the "W" shape. This arrangement may advantageously make it easier for the person to grasp the object, since the gripping portion acts as a mitten. It is noted that the gripping portion of the handling portion 404 may be formed or manipulated in other ways. For example, the gripping portion may be formed or manipulated in a manner to form fingers for receiving the fingers of the person's hand extending into the package (e.g., providing for a glove or glove-like second end of the gripping portion).

FIGS. 9A-16C illustrate several exemplary embodiments of cross-sections of flexible multilayer films 205, 1205, 2205, 3205, 305, 1305, 2305, 3305 for use in forming packages, such as, for example, the packages 101, 401. It is noted that the reference numerals for the films shown in FIGS. 9A-16C are changed (e.g., compared to FIGS. 1-5) to convey that any of the differently configured films can be used to form any of the packages disclosed herein. Generally the film used to form the packages of this disclosure is a multilayer film comprising a first film, a second film, a bonding layer, a first release layer and a second release layer. The first film and the second film may comprise a single layer or may be multilayer films.

Figure 9A:
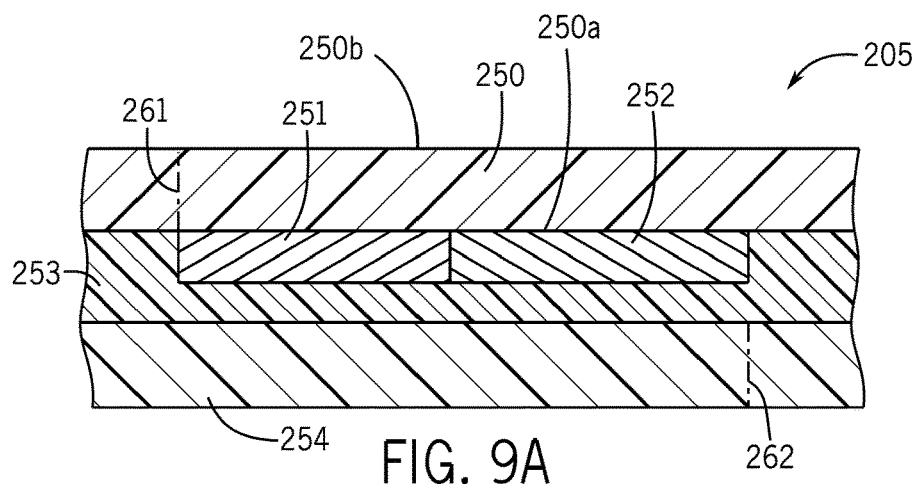
FIG. 9A is a cross-sectional view taken along line 9-9 of FIG. 3 illustrating a first embodiment.
Figure 9B:
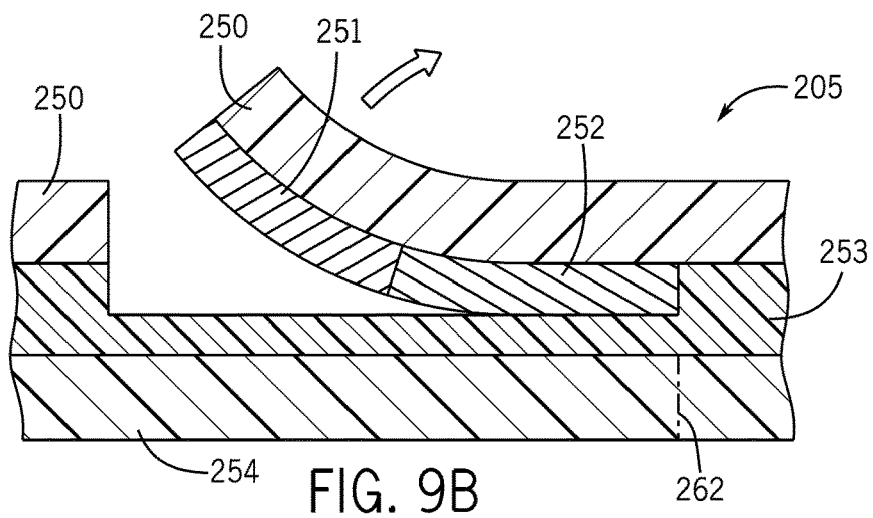
FIG. 9B is the cross-sectional view of the first embodiment shown in FIG. 9A during separation.
Figure 9C:
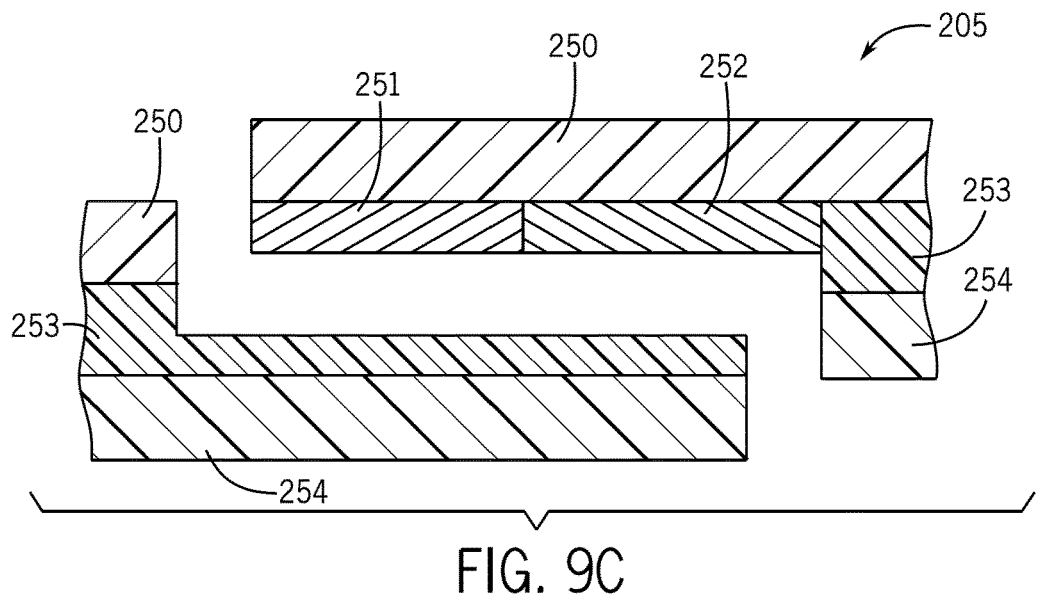
FIG. 9C is the cross-sectional view of the first embodiment shown in FIG. 9A after separation.

FIGS. 9A-9C illustrate a first exemplary embodiment of a flexible multilayer film 205 for use in forming packages, such as the package 101, 401. The film 205 includes a first film 250 (e.g., shown as an exterior film or layer in FIG. 9A), a first release layer 251 analogous to the first release layer 151 shown in FIG. 3 (e.g., a layer including a first release lacquer), a second release layer 252 analogous to the second release layer 152 shown in FIG. 3 (e.g., a layer including a second release lacquer), a bonding layer shown as an adhesive layer 253, and a second film 254 (e.g., an interior film or layer). The film 205 is configured to facilitate separation, such as between the housing portion 102 and the handling portion 104. FIG. 9A illustrates the film 205 prior to separation; FIG. 9B illustrates the film 205 during separation (e.g., peeling of a portion of the first film 250, the first release layer 251 and the second release layer 252); and FIG. 9C illustrates the film 205 after separation (e.g., full separation) of the handling and housing portions.

The first film 250 includes a first surface 250a (e.g., shown in FIG. 9A as a bottom/interior surface configured to face the interior of the package) and a second surface 250b (e.g., shown in FIG. 9A as a top surface configured to face the exterior of the package and being the surface that a user will come into contact with before removing the product, such as during handling of the package) opposite the first surface 250a. The first film 250 may be made from a material that has a relatively high tensile strength and/or chemical stability. The first film 250 may transparent, translucent, or opaque. Some non-limiting examples of materials that may form the first film 250 are biaxially-oriented polyethylene terephthalate (BoPET), biaxially-oriented polypropylene (BOPP), and biaxially-oriented polyamide (BOPA). The first film 250 may have a thickness, which may be tailored to the specific application using the film/package. According to non-limiting examples, the thickness of the first film 250 may be from 42 gauge to 200 gauge. However, it is noted that the first film 250 may be made from other suitable materials and may have a thickness less than or greater than the examples noted herein.

One of the first film 250 and the second film 254 acts as the substrate for forming/making the film 205. In an exemplary manufacturing method, the first film 250 acts as a substrate for forming the film 205. The first release layer 251 is disposed on a first portion (e.g., first part) of the first surface 250a of the first film 250. The first release layer 251 is configured to help facilitate separation of the film 205 by allowing for the initiation of peel, namely to separate two or more portions (e.g., the housing portion 102 and the handling portion 104). Some non-limiting examples of materials that may form the first release layer 251 are release lacquers, varnishes, etc., such as FCGM7A7CP Siegwerk varnish and FSBM1B6DB Siegwerk varnish. The first release layer 251 is configured having a bond strength relative to the bonding layer (e.g., the adhesive 253) that is less than the bonding strength of the second release layer 252 relative to the bonding layer while still being sufficient to maintain the package in a closed position when handled. According to one non-limiting example, the bond strength of the first release layer 251 is less than 100 grams/inch bond strength. According to another example, the bond strength of the first release layer 251 is less than 50 grams/inch bond strength. The bond strength may be measured in accordance with an exemplary test method, such as, for example, in accordance with ASTM F904. According to another example, the bond strength of the first release layer 251 relative to the adhesive 253 is 25-250 grams per inch (compared to easier peel initiation 250-1200 grams. According to other examples, the seal strength of the first release layer is broadly defined by what it takes for the package to be peelable, be less than the seal strength of the second release layer, and remain closed through general use, which can vary based on the product enclosed in the package. It should also be noted that it is generally desirable that the bond strength at portions of the package not including a release layer will be generally higher than the bond strength of a second release layer relative to the bonding layer.

The second release layer 252 is disposed on a second portion (e.g., second part) of the first surface 250a of the first film 250. The second release layer 252 may be adjacent (e.g., juxtaposed) to the first release layer 251, such as shown in FIG. 9A. According to one example, the second release layer 252 is in contact with the first release layer 251. For example, a side surface of the second release layer 252 abuts a side surface of the first release layer 251. This contacting arrangement of the release layers is particularly advantageous when the adhesive layer is able to fill in gaps, such as when the adhesive layer is applied as a liquid. If a gap is provided between the two release layers and a liquid adhesive is applied over the release layers, the adhesive may fill the gap and adhere to the first film behind the release layers, which would negatively impact separation of the film by allowing peeling of the first film only across the first release layer. According to another example, the first and second release layers 251, 252 may be separated from one another by an offset distance (e.g., a gap) if the adhesive layer employed does not fill the offset distance.

The second release layer 252 is configured to help maintain a seal (e.g., hermetic seal) until separation of the film 205, such as the housing portion 102 and the handling portion 104. Some non-limiting examples of materials that may form the second release layer 252 are release lacquers, varnishes, etc., such as FCGM1544 Siegwerk varnish. The second release layer 252 may be configured having a desired (e.g., specific) bond strength. According to one non-limiting example, the bond strength of the second release layer 252 is greater than the bond strength of the first release layer 251. For example, the bond strength of the second release layer 252 may be greater than 100 grams/inch bond strength relative to the bonding layer, here adhesive 253. According to another example, the bond strength of the second release layer 252 is greater than 200 grams/inch bond strength.

As noted, combination of the first release layer and the second release layer provides further benefits in facilitating the separation of the film 205 into a housing portion and a handling portion after the package is formed. The first release layer 251 allows a user to initiate peel separation between a portion of the film (e.g., a portion of the first film 250 and the first release layer 251 as shown in FIG. 9A) from another portion of the film (e.g., another portion of the first film 250, the adhesive 253 and the second film 254 as shown in FIG. 9A) as the user transitions the package from a fully closed package to an open package (e.g., wherein the handling and housing portions have been separated). By having a relatively lower bond strength, the first release layer requires less force application to separate (e.g., peel) than the second release layer. Thus, this further facilitates separation by making peel initiation easier and allowing for a smooth transition to the increased force required to disrupt the hermetic seal and eventually arrive at separation of the housing portion and the handling portion of the package. The relatively higher bond strength of the second release layer 252 allows for the hermetic seal to be maintained. Upon continued peeling of the portion of the film beyond the second release layer 252, the adhesive 253 and second film 254 are configured to separate along the second line of weakness 262 to form the housing portion and the separated handling portion.

The adhesive layer 253 is configured to couple (e.g., secure, bond, etc.) two or more of the layers of the film 205 together. As shown in FIG. 9A, the adhesive layer 253 is disposed between the first film 250 and the second film 254, namely at the handling portion and the housing portion. The adhesive layer 253 also overlaps (e.g., overlays) one side of the release layer 251 and one side of the second release layer 252, namely at the overlapping portion of the handling portion and the housing portion. In other words, the adhesive layer 253 may overlap the first release layer 251 and the second release layer 252 and may be interposed directly between the first film 250 and the second film 254 in other areas.

The adhesive layer 253 may be a continuous (e.g., uninterrupted) layer such that all of the parts of the adhesive layer 253 are interconnected or the adhesive layer 253 may have gaps (e.g., intermittent voids). The adhesive layer 253 may have a uniform thickness throughout the film 205, or may have a thickness that varies, such as between the different parts of the adhesive layer 253. For example, the thickness of the adhesive layer 253 between the first parts of the first film 250 and the second film 254 may be different (e.g., greater, thicker, smaller, thinner, etc.) compared to the thickness of the adhesive layer 253 between the first part of the first release layer 251 and the third part of the second film 254. Also for example, the thickness of the adhesive layer 253 between the second parts of the first film 250 and the second film 254 may be different (e.g., greater, thicker, smaller, thinner, etc.) compared to the thickness of the adhesive layer 253 between the first part of the second release layer 252 and the fourth part of the second film 254. It should be noted that layer sizes and proportions may be exaggerated in the figures for clarity (e.g., a first film and a second film are generally much thicker relative to the release layers and bonding layer than they are shown in the FIGS.).

Some non-limiting examples of materials that may form the adhesive layer 253 are two-part urethane or polyester based adhesives. Other suitable adhesive materials may be included in the adhesive layer 253 to create a sufficient/desirable amount of adhesion between the layers. Moreover, additional intermediate layers may be used.

The second film 254 is located on a side of the first release layer 251 and the second release layer 252 that is opposite the first film 250. The second film 254 and the first film 250 may be configured to sandwich the remaining layers of the film 205 therebetween. As shown in FIG. 9A, the second film 254 is disposed directly on the adhesive layer 253. Some non-limiting examples of materials that may form the second film 254 or that the second film 254 may include are sealant materials, such as ethylene-vinyl acetate (EVA) (e.g., polyethylene-vinyl acetate (PEVA)), low-density polyethylene (LDPE), linear low-density polyethylene (LLDPE), as well as other sealant films.

Other examples of materials that may be used for a first film or a second film include polyethylene, polypropylene, other polymers, as well as non-polymeric materials such as foils, papers, etc. The thickness of each film may be tailored to the design application, such as the weight or shape of the product(s) to be housed in the package (e.g., the package 101). According to one non-limiting example, the thickness of the film is approximately 2 to 6 mils. Also for example, a multilayer film structure could advantageously be configured to act as an oxygen barrier, a moisture barrier, a static barrier (e.g., anti-static), or provide other useful properties.

The first release layer 251 and the second release layer 252 are configured to facilitate the separation of film 205, such as, the package (e.g., the package 101, 401) that is made using the film (e.g., the film 205, 305, etc.). For example, the release layers 251, 252 may facilitate separation of the housing portion 102 and the handling portion 104. Accordingly, the separation feature 106 may include the first release layer 251 and/or the second release layer 252.

The film 205 may include one or more than one line of weakness to help facilitate separation of the film 205 and/or the package formed from the film 205. As shown in FIG. 9A, the film 205 includes a first line of weakness 261 that extends through at least a portion of the first film 250 toward the first release layer 251 and a second line of weakness 262 that extends through at least a portion of the second film 254 toward the second release layer 252. According to an exemplary embodiment, each line of weakness 261, 262 extends all the way through the thickness of the associated layer (e.g., the first film 250, the second film 254). According to other examples, each line of weakness 261, 262 may extend through less than all of the thickness of the associated layer.

Each line of weakness 261, 262 may extend along the associated layer in a continuous manner (e.g., as a continuous or uninterrupted channel or region of decreased thickness extending around the circumference of the package, etc.). For example, the first line of weakness 261 may be configured to extend along a length of the first film 250 without interruption. The first film 250 may include an inner surface (e.g., the first surface 250a) that is adjacent to (e.g., in contact with) one of the release layers and/or the adhesive layer 253 and an outer surface (e.g., the second surface 250b) that is opposite the inner surface. The first line of weakness 261 may extend along a distance (e.g., the width) of the outer surface of the first film 250 without interruption. Similarly, the second film 254 may include an inner surface that is adjacent to (e.g., in contact with) the adhesive layer 253 and an outer surface that is opposite the inner surface. The second line of weakness 262 may extend along the length of the outer surface of the second film 254 without interruption. For example, each continuous line of weakness 261, 262 may be scored, such as using a laser, a blade, or any other suitable process.

Each line of weakness 261, 262 may extend along the associated layer in an interrupted manner (e.g., non-continuously, intermittent, discontinuous regions of decreased thickness, such as a series of adjacent indentations or openings in the material, etc.), such as along a depth (e.g., thickness) and/or a length (e.g., transverse to the thickness) to provide a series of steps (e.g., notches, etc.) in the film. For example, each line of weakness 261, 262 may be configured as a perforation (e.g., a series of holes). Also for example, each perforated line of weakness 261, 262 may be scored, such as using a laser, a blade (e.g., a perforation blade), or any other suitable process. If the scoring is intermittent, such as from pulsing the laser, the length of each score and the distance between successive scorings may be tailored to the design application, such as to allow separation at a desired force.

For packages configured to help provide for a sterile/aseptic presentation of a product, the scoring may be configured to extend through the thickness of a first film or a second film. Such a configuration helps provide for a clean separation of the housing portion and the handling position (e.g., avoiding an extra tug or pull to achieve full separation). The use of a laser to score the film may advantageously provide for greater control and/or more precision with respect to the scoring process. For example, the laser may be configured (e.g., by adjusting its frequency) to remove only certain layers of the film (e.g., first film, second film, etc.) or only portions of certain layers. By way of example, if the material of the film includes more than one layer of different types of materials (e.g., a layer of nylon, a layer of polyethylene), then the laser can be configured to remove only select portions of one (or more than one) layer while leaving one (or more than one) other layer to maintain the sterile/aseptic presentation. Generally, it is desirable to avoid extension of the scoring into the release layers so as not to compromise sterility or increase the likelihood of such a compromise.

According to an exemplary embodiment, the first line of weakness 261 is aligned substantially with the first release layer 251, such that the first line of weakness 261 overlies the first release layer 251. For example, the first line of weakness 261 may be substantially aligned with a side/edge of the first release layer 251. As shown in FIG. 9A, the first line of weakness 261 is aligned substantially with an outer side/edge of the first release layer 251 that is opposite an inner side/edge of the first release layer 251 that is proximate (e.g., abutting) the second release layer 252. Also shown, the first line of weakness 261 extends through the first film 250, but does not extend into the first release layer 251 or the adhesive layer 253.

According to an exemplary embodiment, the second line of weakness 262 is aligned substantially with the second release layer 252, such that the second line of weakness 262 overlies the second release layer 252. For example, the second line of weakness 262 may be substantially aligned with a side/edge of the second release layer 252. As shown in FIG. 9A, the second line of weakness 262 is aligned substantially with an outer side/edge of the second release layer 252 that is opposite an inner side/edge of the second release layer 252 that is proximate (e.g., abutting) the first release layer 251. Also shown, the second line of weakness 262 extends through the second film 254, but does not extend into the adhesive layer 253 or the second release layer 252.

Accordingly, the separation feature 106 may include the first line of weakness 261 and/or the second line of weakness 262. The first line of weakness 261 may facilitate separation of the first film 250 at the location of the first line of weakness 261. The first line of weakness 261 may help separate other layers of the film 205 as well either alone, or in combination with one or more of the release layers. The second line of weakness 262 may facilitate separation of the second film 254 at the location of the second line of weakness 262. The second line of weakness 262 may help separate other layers of the film 205 as well either alone, or in combination with one or more of the release layers.

Each line of weakness (e.g., of the separation feature) may be formed using other mechanical techniques for cutting and/or scoring, and the techniques disclosed herein are intended to be exemplary and not limiting.

Each film (e.g., the film 205, etc.) can be made using various exemplary embodiments of manufacturing methods/techniques/processes. For example, each film may be made using an adhesive press lamination process (e.g., using an adhesive press laminator, using a printing press followed by adhesive laminator, etc.). As another example, each film may be made using an extrusion press lamination process (e.g., using an extrusion press laminator, using a printing press followed by an extrusion laminator, etc.).

According to one exemplary method, a film (e.g., the film 205) can be made using a four step process. Although the below four steps may be described below using sequential terms (e.g., first, second, third, etc.), the order of the steps can be rearranged (e.g., switched) according to one of skill in the art of packages.

One step of the method (e.g., the first step) includes providing a base film (e.g., the first film 250, the second film 252). Utilizing the first film 250 for this example, the base layer includes the first (e.g., inner) surface 250a and the second (e.g., outer) surface 250b that is opposite the first surface 250a. The base layer can be configured according to any of the embodiments disclosed herein, such as, for example, the first film 250 of the film 205.

Another step of the method (e.g., the second step) includes providing (e.g., pattern applying) one or more than one release layer onto the base layer. As shown in FIG. 9A, the second step includes disposing the first release layer 251 on a first part of the first surface 250a of the first film 250 and disposing the second release layer 252 on a second part of the first surface 250a of the first film 250. The second part of the first surface can be located adjacent to the first part of the first surface, such that the second release layer 252 is adjacent (e.g., juxtaposed) to the first release layer 251.

Another step of the method (e.g., the third step) includes providing the adhesive layer onto the film. As shown in FIG. 9A, the adhesive layer 253 can be applied over the first film 250, the first release layer 251, and the second release layer 252. For example, the adhesive layer 253 can be applied in flood coat that covers the entire exposed surface of the first film 250, the entire exposed surface of the first release layer 251 and the entire exposed surface of the second release layer 252. The application of the adhesive layer 253 can be performed as another operation (e.g., in another tool or machine) or as a continuation of the second step (e.g., in the same tool or machine).

Another step of the method (e.g., the fourth step) includes providing another layer (e.g., the second film 254, another polymeric layer, etc.) onto the film. As shown in FIG. 9A, the second film 254 is disposed on (e.g., laminated to) the film 205 (e.g., at the flood coated adhesive layer 253), which is secured together using the adhesive.

According to other embodiments, the film (e.g., the film 205) may include additional layers, such as an intermediate layer that is provided between the second film 254 and the adhesive layer 253. In embodiments where the bonding layer is a polymer extrudate, the intermediate layer may, for example, be or include a primer as will be discussed in more detail below.

FIG. 9B shows the cross-section of the film 205 (shown in FIG. 9A) during separation (e.g., delamination, uncoupling, peeling, etc.), such as to provide access to a product (e.g., the product 99). FIG. 9C shows the cross-section of the film 205 (shown in FIG. 9A) after separation (e.g., delamination, peeling, etc.), with the product 99 accessible. As shown in FIG. 9C, the first film 250 separates at the first line of weakness 261 and the second film 254 and the adhesive layer 253 separate at the second line of weakness 262. The first and second release layers 251, 252 separate from the adhesive layer 253 and remain with the first and second parts of the first film 250. After separation, the handling portion and housing portions may be two distinct (e.g., stand alone, separated, etc.) elements. For example, the portion of the film 205 having the first and second release layers 251, 252 may form the housing portion or the handling portion.

Figure 10A:
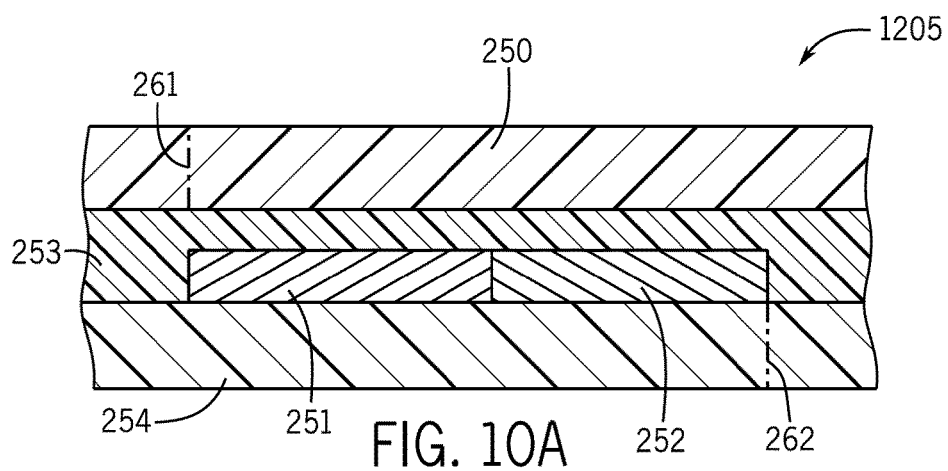
FIG. 10A is a cross-sectional view taken along line 9-9 of FIG. 3 illustrating a second embodiment.
Figure 10B:
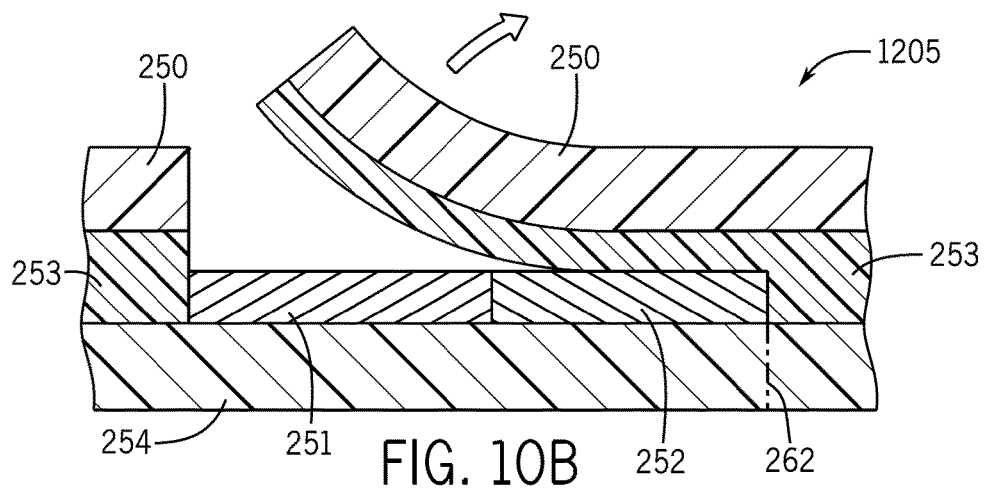
FIG. 10B is the cross-sectional view of the second embodiment shown in FIG. 10A during separation.
Figure 10C:
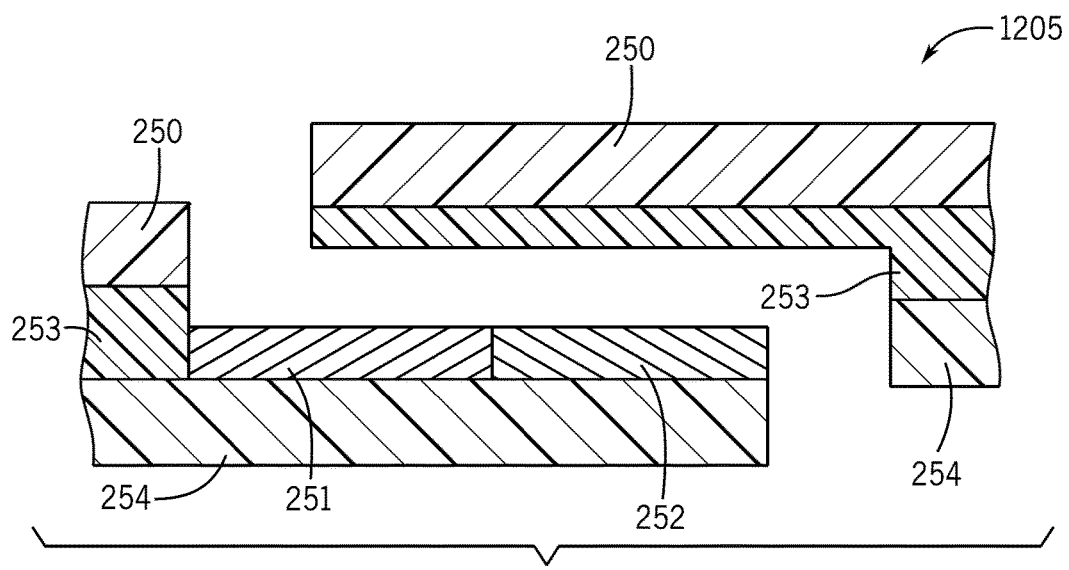
FIG. 10C is the cross-sectional view of the second embodiment shown in FIG. 10A after separation.

FIGS. 10A-10C illustrate another exemplary embodiment of a flexible multilayer film 1205 for use in forming packages, such as the package 101. FIG. 10A illustrates the film 1205 before separation (e.g., of the handling and housing portions). FIG. 10B illustrates the film 1205 during separation as a portion of the first film 250 and the adhesive 253 are peeled from adjacent portions of the first film 250 and the adhesive 253 as well as the first and second release layers 251, 252. FIG. 10C illustrates the film 1205 after separation (e.g., of the handling and housing portions). The construction of the film 1205 is identical to the construction of the film 205, except the first and second release layers 251, 252 of the film 1205 are applied to the second film 254 (e.g., the interior layer of the second film) rather than to the first film 250 (e.g., the exterior layer) as with the film 205. This change in configuration of the film 1205 leads to a change in separation, as illustrated in FIG. 10C. As shown, the first and second release layers 251, 252 of the film 1205 remain with the parts (e.g., portions) of the second film 254 to which the release layers 251, 252 are applied.

Figure 11A:
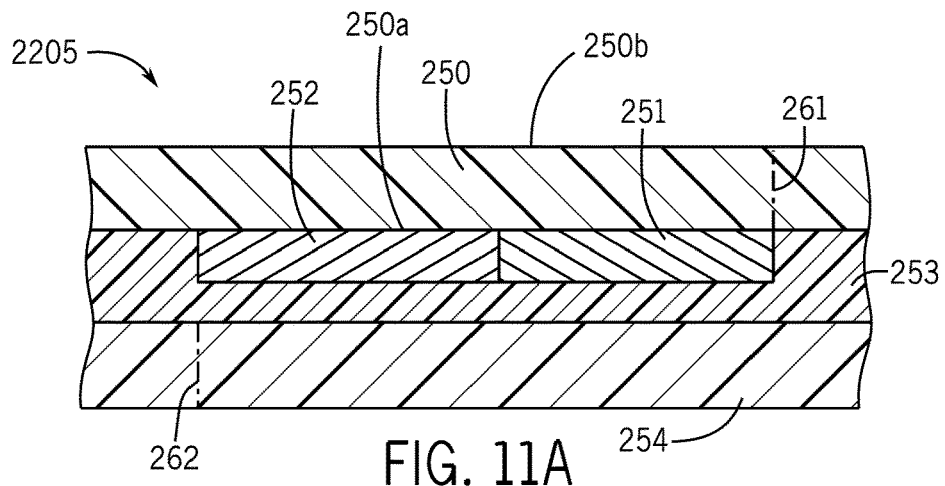
FIG. 11A is a cross-sectional view taken along line 9-9 of FIG. 3 illustrating a third embodiment.
Figure 11B:
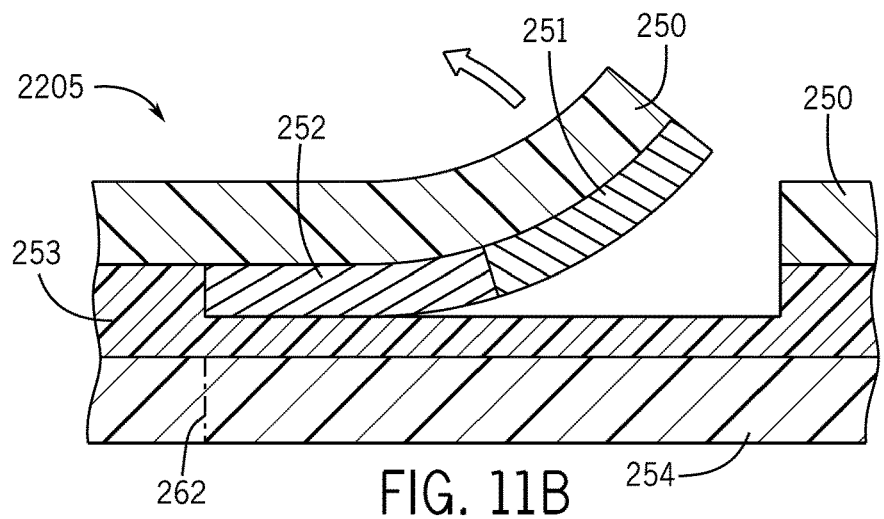
FIG. 11B is the cross-sectional view of the third embodiment shown in FIG. 11A during separation.
Figure 11C:
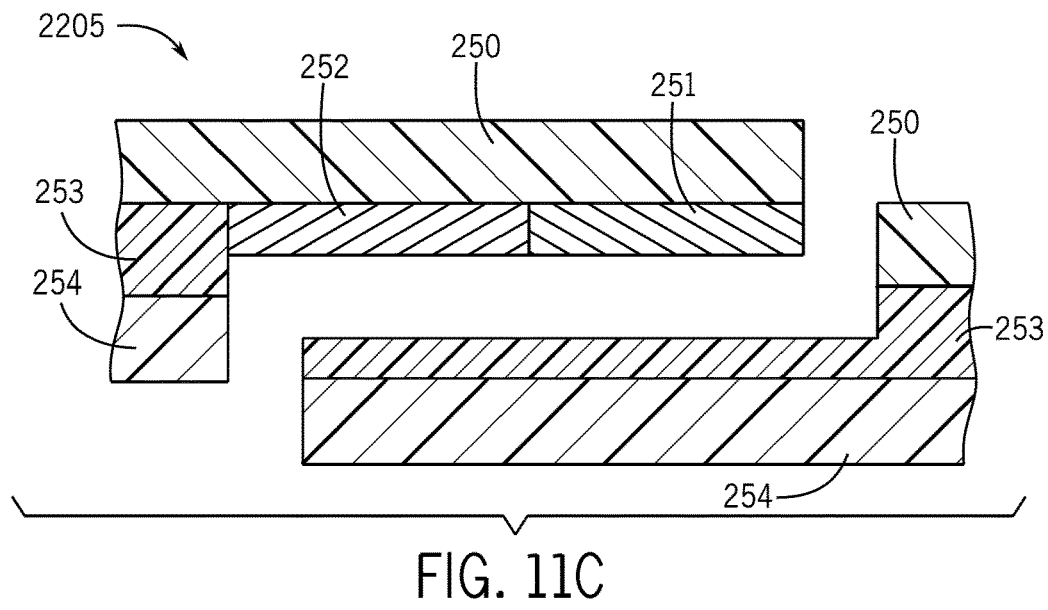
FIG. 11C is the cross-sectional view of the third embodiment shown in FIG. 11A after separation.

FIGS. 11A-11C illustrate another exemplary embodiment of a flexible multilayer film 2205 for use in forming packages, such as the package 101. FIG. 11A illustrates the film 2205 before separation (e.g., of the handling and housing portions). FIG. 11B illustrates the film 2205 during separation as a portion of the first film 250, the first release layer 251 and the second release layer 252 are peeled (in a different direction compared to the film 205 shown in FIG. 9B) from adjacent portions of the first film 250, the adhesive 253 and the second film 254. FIG. 11C illustrates the film 2205 after separation (e.g., of the handling portion and the housing portion). The construction of the film 2205 is identical to the construction of the film 205, except the locations of the first and second release layers 251, 252 of the film 1205 are switched and the locations of the first and second lines of weakness 261, 262 are moved to be adjacent to the first and second release layers 251, 252, respectively. This change allows for the film 2205 to be separated by peeling from a different direction relative to the housing portion and handing portion than that shown for the film 205. For example, the film 205 may be configured such that a portion of the handling portion is peeled away from the housing portion and the film 2205 may be configured such that a portion of the housing portion is peeled away from the handling portion. Thus, the portion being peeled in FIG. 9B is a portion of the handling portion, which is being peeled off of (e.g., generally away from, etc.) the housing portion; and the portion being peeled in FIG. 11B is a portion of the housing portion, which is being peeled off of (e.g., generally away from, etc.) the handling portion. It should be noted, in both cases, the films 205 and 2205 are both desirably separated by virtue of initiating peel at the first release layer and applying a force in the direction pulling towards the second release layer; depending on the position of the first release layer and the second release layer, this may be toward or away from the body of person using the gripping portion of the handling portion of the package (assuming the person is positioned generally behind the gripping portion with the package in front of them, extending generally away from his/her body).

Figure 12A:
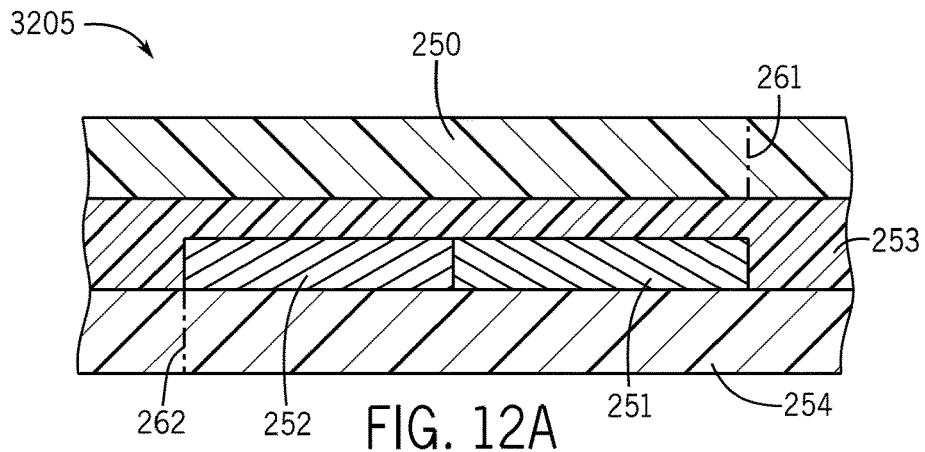
FIG. 12A is a cross-sectional view taken along line 9-9 of FIG. 3 illustrating a fourth embodiment.
Figure 12B:
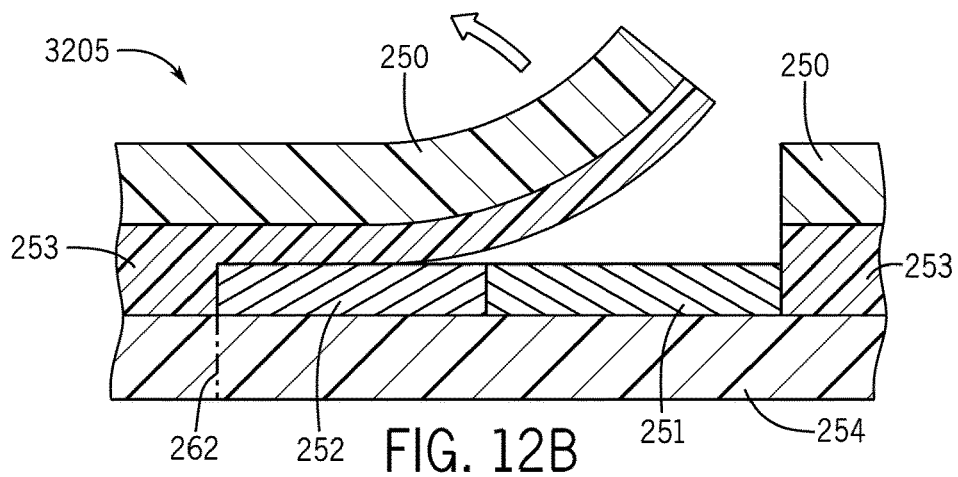
FIG. 12B is the cross-sectional view of the fourth embodiment shown in FIG. 12A during separation.
Figure 12C:
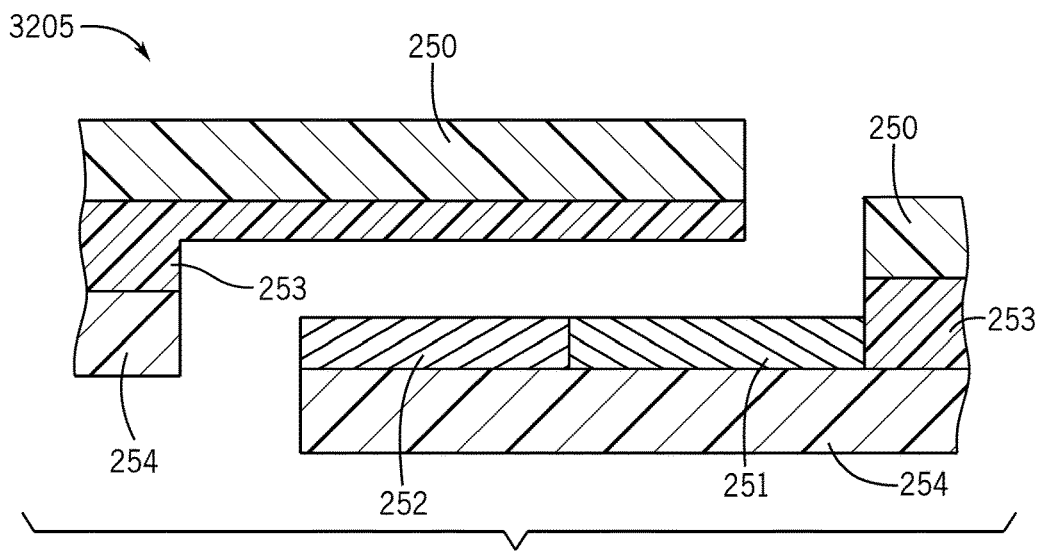
FIG. 12C is the cross-sectional view of the fourth embodiment shown in FIG. 12A after separation.

FIGS. 12A-12C illustrate another exemplary embodiment of a flexible multilayer film 3205 for use in forming packages, such as the package 101. FIG. 12A illustrates the film 3205 before separation (e.g., of the handling and housing portions). FIG. 12B illustrates the film 3205 during separation as a portion of the first film 250 and the adhesive 253 are peeled from adjacent portions of the first film 250 and the adhesive 253 as well as the first release layer 251, the second release layer 252 and the second film 254. FIG. 12C illustrates the film 3205 after separation (e.g., of the handling and housing portions). The construction of the film 3205 is identical to the construction of the film 1205, except the locations of the first and second release layers 251, 252 of the film 1205 are switched and the locations of the first and second lines of weakness 261, 262 are moved to be adjacent to the first and second release layers 251, 252, respectively. This change allows for the film 2205 to be peeled from a different direction (relative to the housing portion and handling portion) than the film 1205. For example, the film 1205 may be configured such that a portion of the handling portion is peeled away from the housing portion and the film 3205 may be configured such that a portion of the housing portion is peeled away from the handling portion. Thus, the portion being peeled in FIG. 10B is a portion of the handling portion, which is being peeled off of (e.g., generally away from, etc.) the housing portion; and the portion being peeled in FIG. 12B is a portion of the housing portion, which is being peeled off (e.g., generally away from, etc.) of the handling portion.

Figure 13A:
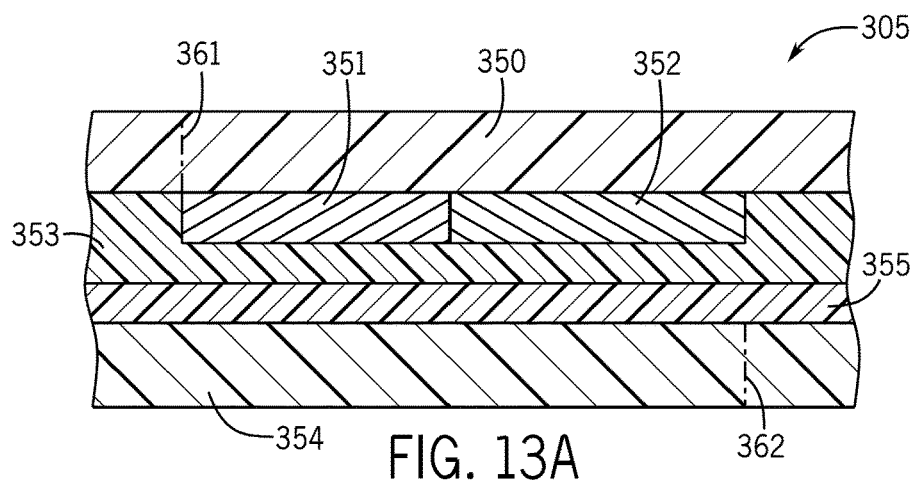
FIG. 13A is a cross-sectional view taken along line 9-9 of FIG. 3 illustrating a fifth embodiment.
Figure 13B:
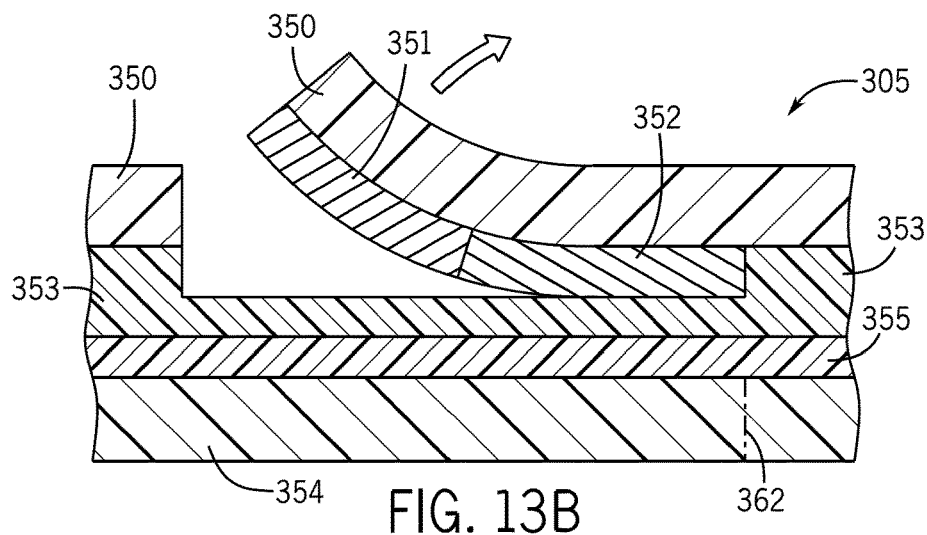
FIG. 13B is the cross-sectional view of the fifth embodiment shown in FIG. 13A during separation.
Figure 13C:
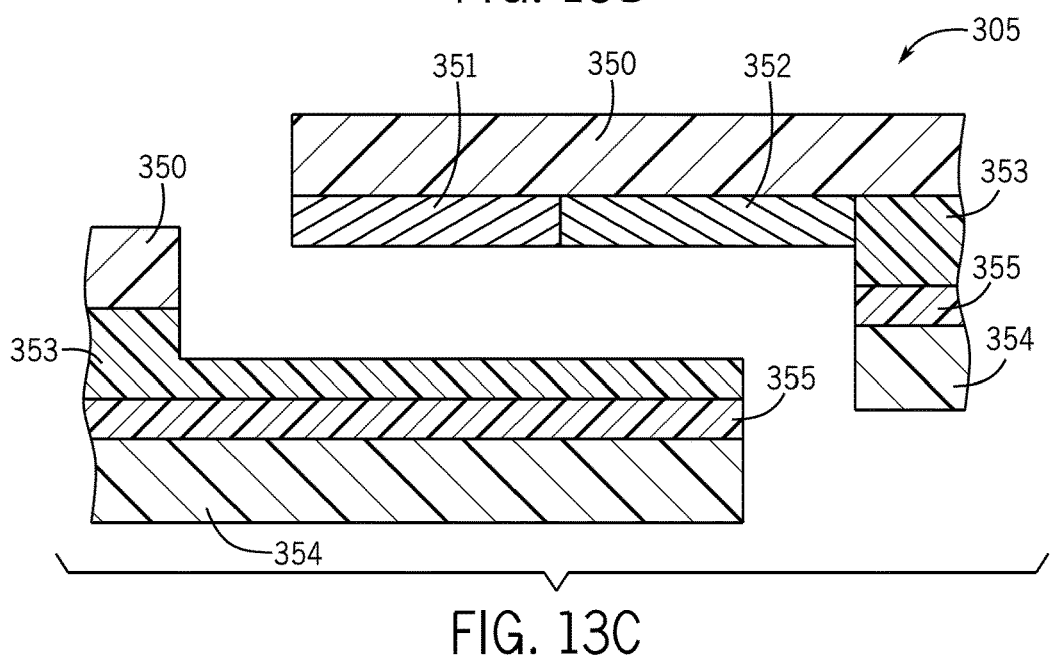
FIG. 13C is the cross-sectional view of the fifth embodiment shown in FIG. 13A after separation.

FIGS. 13A-13C illustrate another exemplary embodiment of a flexible multilayer film 305 for use in forming packages, such as the package 101. FIG. 13A illustrates the film 305 before separation (e.g., of the handling and housing portions). FIG. 13B illustrates the film 305 during separation as a portion of the film 305 is peeled from another portion of the film 305. FIG. 13C illustrates the film 305 after separation (e.g., of the handling and housing portions).

The film 305 includes a first film 350 (e.g., shown as an exterior film or layer in FIG. 13A), a first release layer 351 analogous to the first release layer 151 shown in FIG. 3 (e.g., a layer including a first release lacquer), a second release layer 352 analogous to the second release layer 152 shown in FIG. 3 (e.g., a layer including a second release lacquer), a bonding layer including an extrudate layer 355 (e.g., shown as an intermediate layer in FIG. 13A), a second film 354 (e.g., shown as an interior film or layer in FIG. 13A). The bonding layer of the film 305 may optionally include a primer layer (e.g., an extruded primer layer, such as a flood coated extrusion primer). As shown in FIGS. 13A-13C, the bonding layer includes both the extrudate layer 355 and a primer layer 353, with the primer layer 353 overlying the first film 350, the first release layer 351 and the second release layer 352 and with the extrudate layer 355 interposed (e.g., provided between) the second film 354 and the primer layer 353. According to one exemplary embodiment, each of the first film 350, the first release layer 351, the second release layer 352, and the second film 354 of the film 305 are configured the same as or substantially the same as the first film 250, the first release layer 251, the second release layer 252, and the second film 254 of the film 205, respectively, except where noted.

As shown, one difference in the film 305 (as compared to the film 205) is the presence of an extrudate layer 355 rather than an adhesive layer to bond the multiple layers of the film 305. Another such difference is the presence of the primer layer 353, if provided, which is located between the extrudate layer 355 and the first film 350. The extrudate layer 355 may, for example, include a polymer extrudate, such as an LDPE. The extrudate layer 355 may be applied to the primer layer 353, such as a molten polymer extrudate, or may be applied directly to the first film and release layers. Some non-limiting examples of materials that may form the primer layer are polyethylenimine (PEI) primers. For example, the primer layer may include water based PEI primers, such as a one-part water based PEI primer. Other suitable materials may be included in the primer layer to create a sufficient/ desirable amount of adhesion between the layers. Moreover, additional intermediate layers may be used.

According to another exemplary process, a film (e.g., the film 305, etc.) is made using a five step process. Although the five steps may be described below using sequential terms (e.g., first, second, third, etc.), the order of the steps can be rearranged (e.g., switched) according to one of skill in the art of packages.

One step of the method (e.g., the first step) includes providing a film as a substrate (e.g., the first film 350 or the second film 352). Utilizing the first film 350 as the substrate for this example, the first film includes a first (e.g., inner) surface and a second (e.g., outer) surface that is opposite the first surface. The first film can be configured according to any of the embodiments disclosed herein, such as, for example, the first film 350 of the film 305.

Another step of the method (e.g., the second step) includes providing (e.g., pattern applying) one or more than one release layer onto the first film. As shown in FIG. 13A, the second step includes disposing the first release layer 351 on a first portion (e.g., part) of the first surface of the first film 350 and disposing the second release layer 352 on a second portion of the first surface of the first film 350. The second portion of the first surface can be located adjacent to the first portion of the first surface, such that the second release layer 352 is adjacent (e.g., juxtaposed) to the first release layer 351.

Another step of the method (e.g., the third step) includes providing a primer layer onto the film. For example, a layer of extrusion primer may be applied in a flood coat onto the film. For example, the primer layer 353 can be applied in such a manner over the first film 350, the first release layer 351, and the second release layer 352. The application of the primer layer 353 can be performed as another operation (e.g., in another tool or machine) or as a continuation of the second step (e.g., in the same tool or machine).

Another step of the method (e.g., the fourth step) includes providing a layer of polymer extrudate (e.g., the extrudate layer 355) over the layer of extrusion primer if provided or onto the film if no primer is present. For example, a molten polymer extrudate layer may be applied, as the extrudate layer 355, over the exposed surface (e.g., the top, bottom, etc.) of the primer layer 353 (see FIG. 13A). According to an exemplary embodiment, the third and fourth steps together accomplish providing a bonding layer.

Another step of the method (e.g., the fifth step) includes providing the second film onto the film. For example, the second film 354 may be disposed onto (e.g., laminated to) the extrudate layer 355 of the film 305 (see FIG. 13A). Thus, the combination of the primer and extrudate bond/secure the first film and second film.

FIG. 13C shows the cross-section of the film 305 after separation (e.g., delamination, peeling, etc.), such as to provide access to a product (e.g., the product 99) contained within. As shown in FIG. 13B, the first film 350 and the first release layer separate at the first line of weakness 361 when peeled away from the lower layers of the film, while the second film 354, extrudate layer 355 and the primer layer 353 separate at the second line of weakness 362 as the second release layer 252 is peeled from the bonding layer. The first and second release layers 351, 352 separate from the bonding layer and remain with the first and second portions of the first film 350. This separation may form the handling and housing portions for a package. For example, the portion of the film 305 having the first and second release layers 351, 352 may form one of the housing portion and the handling portion.

An as alternative to one or more of the steps (e.g., third, fourth, fifth, etc.) of the process directly above, the process may include providing a film (e.g., the second film 354) that has been premade (e.g., pretreated, preformed, etc.) with a chemical to promote extrusion lamination. Similarly, the first film (e.g., first film 350) may be premade with a chemical to promote extrusion lamination to change (e.g., reduce) the steps noted above.

Figure 14A:
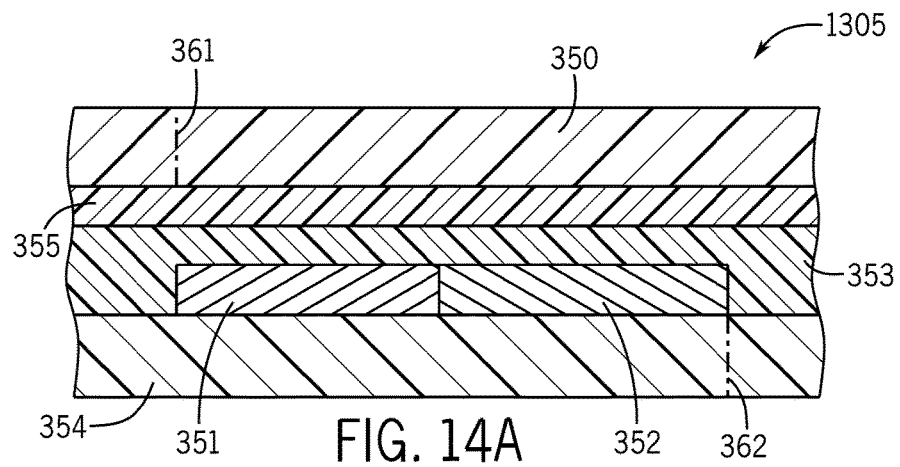
FIG. 14A is a cross-sectional view taken along line 9-9 of FIG. 3 illustrating a sixth embodiment.
Figure 14B:
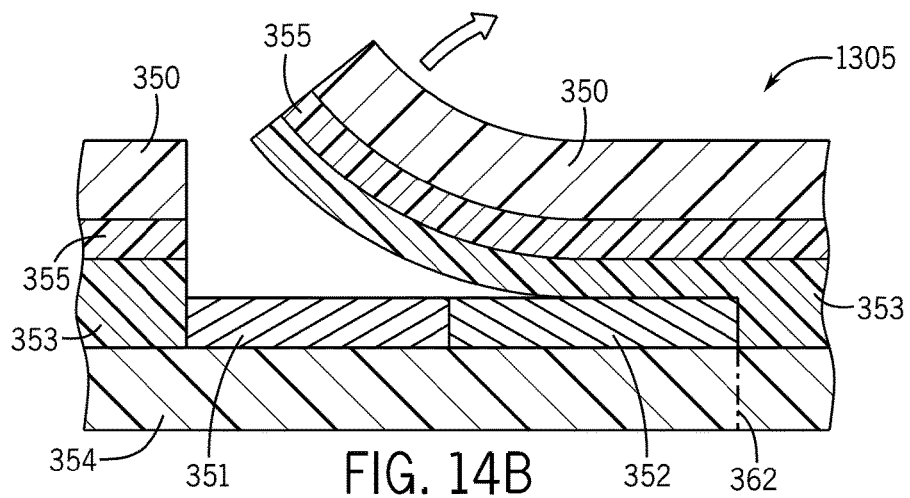
FIG. 14B is the cross-sectional view of the sixth embodiment shown in FIG. 14A during separation.
Figure 14C:
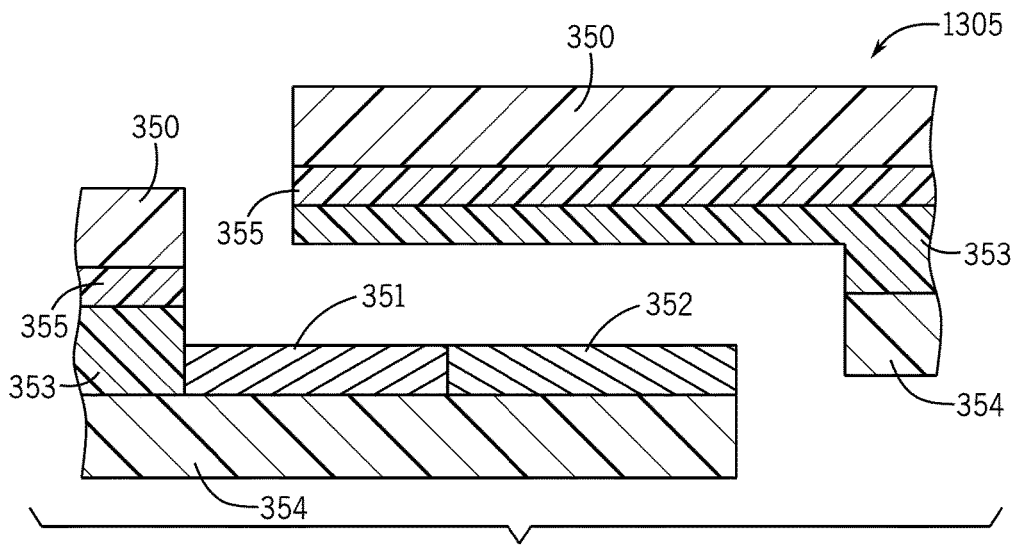
FIG. 14C is the cross-sectional view of the sixth embodiment shown in FIG. 14A after separation.

FIGS. 14A-14C illustrate yet another exemplary embodiment of a flexible multilayer film 1305 for use in forming packages, such as the package 101. FIG. 14A illustrates the film 1305 before separation (e.g., of the handling and housing portions). FIG. 14B illustrates the film 1305 during separation, as a portion of the first film 350 and the bonding layer (e.g., the extrudate layer 355, the primer layer 353) are peeled from the first and second release layers 351, 352, which remain with the second film 354. FIG. 14C illustrates the film 1305 after separation (e.g., of the handling and housing portions).

The construction of the film 1305 is identical to the construction of the film 305, except the first and second release layers 351, 352 of the film 1305 are applied to the second film 354 (e.g., the interior layer, such as first and second parts thereof) rather than to the first film 350 (e.g., the exterior layer) as with the film 305. This change in configuration of the film 1305 leads to a change in separation, as illustrated in FIGS. 14B and 14C, that differs than that of the film 305 (shown in FIGS. 13B and 13C). As shown, the first and second release layers 351, 352 of the film 1305 remain with the first and second portions of the second film 354 that the release layers are applied to, respectively, and the first and second release layers 351, 352 of the film 1305 are separated from the portions of the first film 350 of the film 1305 that correspond to the first and second parts of the first film 350 of the film 305.

Figure 15A:
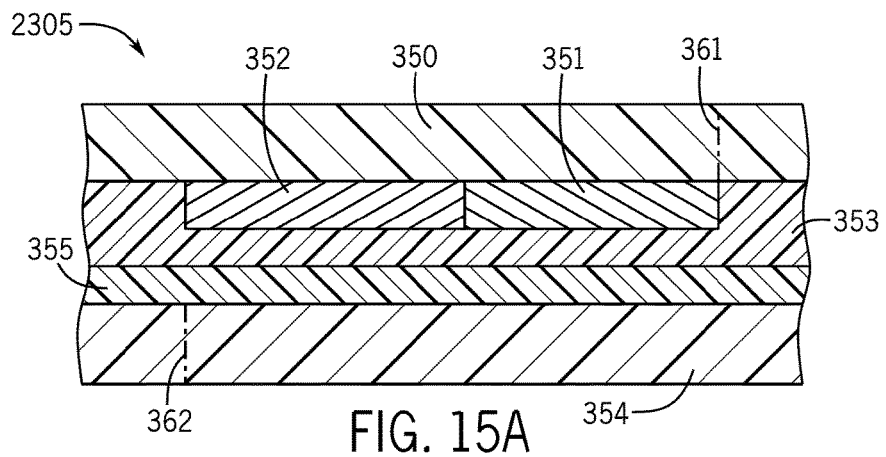
FIG. 15A is a cross-sectional view taken along line 9-9 of FIG. 3 illustrating a seventh embodiment.
Figure 15B:
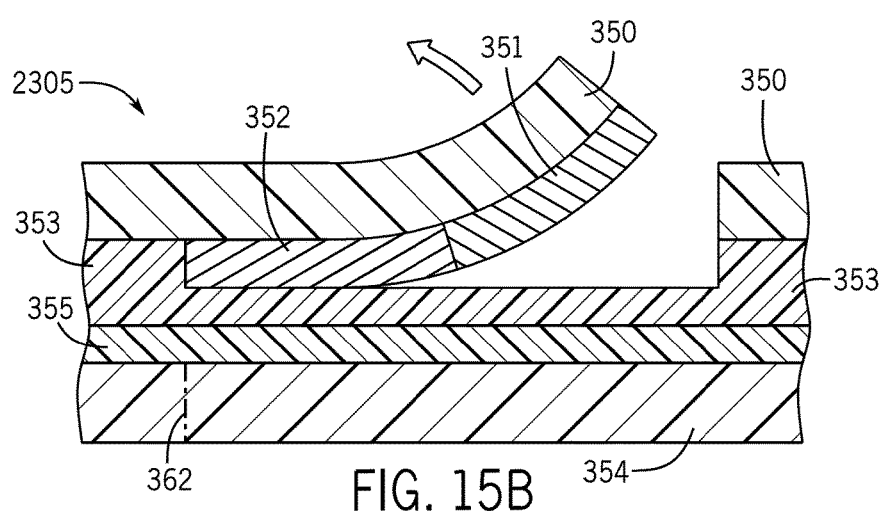
FIG. 15B is the cross-sectional view of the seventh embodiment shown in FIG. 15A during separation.
Figure 15C:
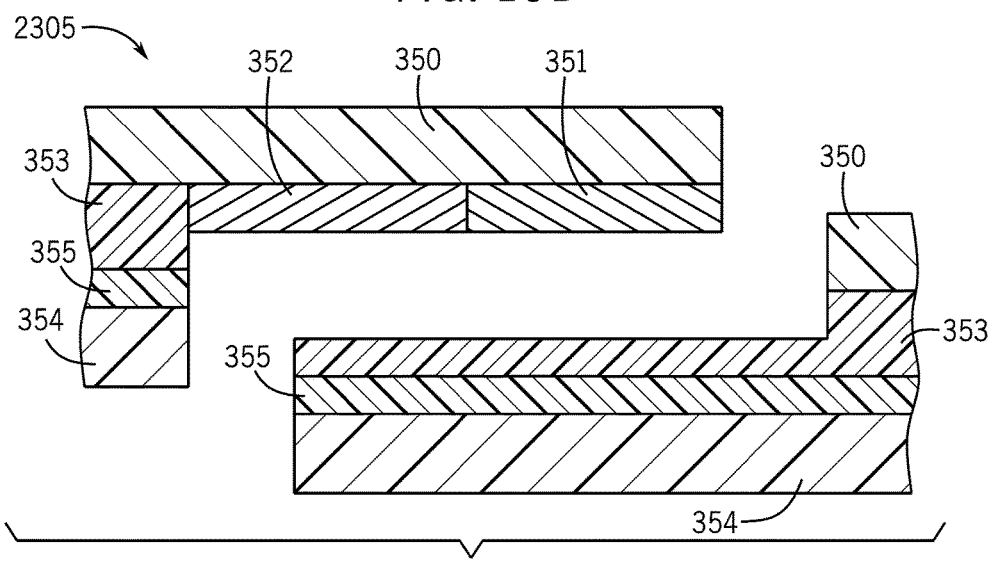
FIG. 15C is the cross-sectional view of the seventh embodiment shown in FIG. 15A after separation.

FIGS. 15A-15C illustrate another exemplary embodiment of a flexible multilayer film 2305 for use in forming packages, such as the package 101. FIG. 15A illustrates the film 2305 before separation (e.g., of the handling and housing portions). FIG. 15B illustrates the film 2305 during separation as a portion of the first film 350, the first release layer 351 and the second release layer 352 are peeled (in a different direction compared to the film 305 shown in FIG. 13B when direction is considered relative to the housing and handling portions) from adjacent portions of the first film 350, the bonding layer and the second film 354. FIG. 15C illustrates the film 2305 after separation (e.g., of the handling and housing portions). The construction of the film 2305 is identical to the construction of the film 305, except the locations of the first and second release layers 351, 352 of the film 2305 are switched and the locations of the first and second lines of weakness 361, 362 are moved to be adjacent to the first and second release layers 351, 352, respectively. This change allows for the film 2305 to be peeled from/in a different direction than the film 305 (relative to the housing and handling portions). For example, the film 305 may be configured such that a portion of the handling portion is peeled away from the housing portion and the film 2305 may be configured such that a portion of the housing portion is peeled away from the handling portion. Thus, the portion being peeled in FIG. 13B is a portion of the handling portion, which is being peeled off of the housing portion; and the portion being peeled in FIG. 15B is a portion of the housing portion, which is being peeled off of the handling portion.

FIGS. 16A-16C illustrate another exemplary embodiment of a flexible multilayer film 3305 for use in forming packages, such as the package 101. FIG. 16A illustrates the film 3305 before separation (e.g., of the handling and housing portions). FIG. 16B illustrates the film 3305 during separation as a portion of the first film 350 and the bonding layer are peeled from adjacent portions of the first film 350 and the bonding layer, as well as from the first release layer 351, the second release layer 352 and the second film 354. FIG. 16C illustrates the film 3305 after separation (e.g., of the handling and housing portions). The construction of the film 3305 is identical to the construction of the film 1305, except the locations of the first and second release layers 351, 352 of the film 3305 are switched and the locations of the first and second lines of weakness 361, 362 are moved to be adjacent to the first and second release layers 351, 352, respectively. This change allows for the film 3305 to be peeled from/in a different direction than the film 1305 (relative to the housing and handling portions). For example, the film 1305 may be configured such that a portion of the handling portion is peeled away from the housing portion and the film 3305 may be configured such that a portion of the housing portion is peeled away from the handling portion. Thus, the portion being peeled in FIG. 14B is a portion of the handling portion, which is being peeled off of the housing portion; and the portion being peeled in FIG. 16B is a portion of the housing portion, which is being peeled off of the handling portion.

It should be noted that any one of the packages disclosed herein (e.g., the package 101 shown in FIGS. 1-5, the package 401 shown in FIGS. 6-8, etc.) may be configured according to any one of the examples shown in FIGS. 9A-16C. In other words, any package disclosed herein may have a cross-sectional configuration according to any disclosed herein. For example, although the package 401 shown in FIGS. 6-8 is configured to have a portion of the handling portion peeled from the housing portion, the package 401 can be reconfigured to have the reverse configuration, in which the housing portion is peeled from the handling portion, such as, for example, according to the examples shown in FIGS. 11B, 12B, 15B, and 16B.

FIGS. 17 and 18 illustrate exemplary embodiments of films 405, 505 laid flat (e.g., generally planar) prior to forming the films into a package. Each of the films 405, 505 may be multilayer structures, such as any multilayer structure disclosed herein (e.g., the films 205, 305).

As shown in FIG. 17, the multilayer film 405 includes a first release layer 451 and a second release layer 452 disposed between (e.g., interposed) a first film 450 and a second film 454 (note that second film 454 is on top of the first film 450 in FIG. 17, which is illustrated by the dashed lead line to reference numeral 450). The release layers 451, 452 may extend between edges of sides (e.g., the edge of the top side and the edge of the bottom side, as shown in FIG. 17). A bonding layer including an adhesive or an extrudate layer may be used to couple the multiple layers of the film 405 together. The film 405 also includes a first line of weakness 461 located at an outer edge of the first release layer 451 and a second line of weakness 462 located at an outer edge of the second release layer 452.

According to an exemplary embodiment, the film 405 may be formed into a package by folding the film 405 along a fold line 470, such that a first edge 471 and a second edge 472 come into contact and two portions 473a, 473b of a third edge come into contact. Then, the first edge 471 and the second edge 472 of the film 405 may be sealed together, such as using a heat sealing process (e.g., sealing through the application of heat and/or pressure). The first portion 473a and the second portion 473b of the third edge may be sealed together, such as using a heat sealing process. Other suitable processes may be used to form each seal. For example, each seal may be formed using an ultrasonic welding process.

The fourth edge 474 of the film 405 may be left open, such that the film 405 forms a package having three sealed sides (coupled sides 471/472, folded side 470, and coupled sides 473a/473b) and one open side (e.g., perimeter formed by edge 474) through which a product can be inserted. After the product is in the internal cavity, the open side can be sealed, and if the package is to provide a sterile/aseptic presentation, the package can be sterilized. As non-limiting examples, the package can be gamma irradiated, exposed to ethylene oxide, or any other suitable sterilization process. Such sterilization process will generally be performed after a product is placed into the package.

As shown in FIG. 18, the multilayer film 505 includes first and second strips 551a, 551b of a first release layer 551 and first and second strips 552a, 552b of a second release layer 552 disposed between (e.g., interposed) a first film 550 and a second film 554 (note that second film 554 is on top of the first film 550 in FIG. 18, which is illustrated by the dashed lead line to reference numeral 550). An adhesive and/or an intermediate layer may be used to couple the multiple layers of the film 505 together. Also, while these strips of the release layers are shown having a substantially constant width, it is understood that the shape (and, thus, the resultant profile when in package form) of the strips may vary as discussed above (e.g., in relation to FIGS. 6-8).

The films may be configured having additional release layers (e.g., a third release layer, a fourth release layer, etc.), according to other examples, such as to provide a more gradual change in bond strengths. This arrangement may have a smoother feel to the person separating (e.g., peeling) the portions. By way of example, a multilayer film may be configured having a third release layer, which may be provided between the first and second release layers such as when the third release layer has a bond strength that is between the bond strengths of the first and second release layers. A third release layer may be configured to sandwich the second release layer between the first and third release layers (e.g., when the bond strength of the third release layer is less than the bond strength of the second release layer, and the bond strength of the first release layer is greater than the bond strength of the second release layer; or when the bond strength of the third release layer is greater than the bond strength of the second release layer, and the bond strength of the second release layer is greater than the bond strength of the first release layer). Yet other embodiments of films may be configured having additional release layers as those described herein are not limiting.

The film 505 also includes a first line of weakness having first and second scorings 561a, 561b. The first scoring 561a is located at an outer edge of the first strip 551a of the first release layer 551 and the second scoring 561b is located at an outer edge of the second strip 551b of the first release layer 551. The first and second scorings 561a, 561b of the first line of weakness are configured to overlie (e.g., align with, etc.) one another upon folding one side of the film 505 about the fold line 570 onto the other side of the film 505.

The film 505 also includes a second line of weakness having first and second scorings 562a, 562b. The first scoring 562a is located at an outer edge of the first strip 552a of the second release layer 552 and the second scoring 562b is located at an outer edge of the second strip 552b of the second release layer 552. The first and second scorings 562a, 562b of the second line of weakness are configured to overlie (e.g., align with, etc.) one another upon folding one side of the film 505 about the fold line 570 onto the other side of the film 505.

According to an exemplary embodiment, the film 505 may be formed into a package by folding the film 505 along a fold line 570, such that first and second portions 571a, 571b of a first edge (e.g., top edge) overlie one another and first and second portions 572a, 572b of a second edge (e.g., bottom edge) overlie one another. Then, the first and second portions 571a, 571b may be sealed together to form a first sealed edge, and the first and second portions 572a, 572b may be sealed together to form a second sealed edge. The fold line 570 forms another sealed edge (e.g., a third sealed edge). A fourth edge including a first portion 574a and a second portion 574b may be left open, such that the film 505 forms a package having three sealed sides and one open side through which a product can be inserted into the internal cavity of the package. The open side can be sealed after the package is in the cavity, and if the package is to provide a sterile/aseptic presentation, the package can be sterilized.

An alternative exemplary embodiment of the first and second scorings of the first line of weakness are shown as 561aa and 561bb in FIG. 18 (these are an alternative to, not in addition to, scorings 561a and 561b). As shown, each of the first and second scorings 561aa and 561bb are shown having a generally arcuate shape that extends over (e.g., overlaps) the first and second release layers. First and second scorings 561aa and 561bb show just one example of an alternative profile of a line of weakness as well as highlight that the lines of weakness do not need to have the same profile as the edge of a release layer. Moreover, the first line of weakness (as will be defined by scorings 561aa and 561bb when the package is formed) need not be positioned entirely above the first release layer 551, but, rather, can be positioned over second release layer 552 in part (e.g., extend towards, over, etc.) so long as the first score is positioned over the first release layer in a manner suitable to provide for peel initiation over the first release layer and then extends therefrom generally toward the second release layer.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

The terms "coupled," "connected," and the like, as used herein, mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the FIGURES. Similarly, the terms "first," "second," etc. are intended for differentiation and not to limit any element to a specific order (e.g., assembly sequence, etc.), arrangement (e.g., location) or other limitation; and any such "first," "second," etc. elements may be rearranged (e.g., switched, reordered, repositioned, relocated, etc.). By way of example, the terms "first film" and "second film" do not limit the two films to a sequence (e.g., a "first film" may be assembled prior to a "second film" or a "second film" may be assembled prior to a "second film") or location (e.g., a "first film" may be an interior film, an exterior film, or an intermediate film; and/or a "second film" may be an interior film, an exterior film, or an intermediate film). It should be noted that the orientation of various elements may differ according to other exemplary embodiments, and that such variations are intended to be encompassed by the present disclosure.

The construction and arrangement of the elements of the packages, as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements, the position of elements may be reversed or otherwise varied, and the nature or number of discrete elements or positions may be altered or varied.

Additionally, the word "exemplary" is used to mean serving as an example, instance, or illustration. Any embodiment or design described herein as "exemplary" is not necessarily to be construed as preferred or advantageous over other embodiments or designs (and such term is not intended to connote that such embodiments are necessarily extraordinary or superlative examples). Rather, use of the word "exemplary" is intended to present concepts in a concrete manner. Accordingly, all such modifications are intended to be included within the scope of the present disclosure. Other substitutions, modifications, changes, and omissions may be made in the design, operating conditions, and arrangement of the preferred and other exemplary embodiments without departing from the scope of the appended claims.

Other substitutions, modifications, changes and omissions may also be made in the design, operating conditions and arrangement of the various exemplary embodiments without departing from the scope of the present invention. For example, any element (e.g., film, layer, panel, sheet, line of weakness, seal, etc.) of the packages disclosed in one embodiment may be incorporated or utilized with any other embodiment disclosed herein. Also, for example, the order or sequence of any process or method steps may be varied or re-sequenced according to alternative embodiments. Any means-plus-function clause is intended to cover the structures described herein as performing the recited function and not only structural equivalents but also equivalent structures. Other substitutions, modifications, changes and omissions may be made in the design, operating configuration, and arrangement of the preferred and other exemplary embodiments without departing from the scope of the appended claims.

What is claimed is:

1. A package configured to contain and provide for sterile presentation of a product, the package comprising:
    a housing portion defining an interior product storage cavity and comprising a first part of a first film, a first part of a second film, and a first part of a bonding layer coupling the first part of the first film to the first part of the second film;
    a handling portion configured to extend away from the storage cavity of the housing portion, the handling portion comprising a second part of the first film, a second part of the second film, and a second part of the bonding layer coupling the second part of the first film to the second part of the second film; and
    a separation feature configured to facilitate separation of the handling portion and the housing portion, the separation feature comprising a first release layer and a second release layer in contact with the first release layer provided between the first film and the second film at an overlapping portion of the housing portion and the handling portion.

2. The package of claim 1, wherein the separation feature further comprises:
    a first line of weakness that extends through at least a portion of a thickness of the first film proximate a first end of the overlapping portion of the housing portion and the handling portion; and
    a second line of weakness that extends through at least a portion of a thickness of second film proximate a second end of the overlapping portion of the housing portion and the handling portion.

3. The package of claim 1, wherein the bonding layer comprises an adhesive layer, the adhesive layer disposed between the first film and the second film at the housing portion and at the handling portion, wherein, at the overlapping portion of the housing portion and the handling portion the adhesive layer overlaps one side of the first release layer and the second release layer.

4. The package of claim 1, wherein bonding layer comprises a polymer extrudate that is disposed between the first film and the second film at the housing portion and at the handling portion, and wherein the polymer extrudate overlaps one side of the first release layer and one side of the second release layer at the overlapping portion of the housing portion and the handling portion.

5. The package of claim 4, wherein bonding layer further comprises a primer layer disposed between the polymer extrudate and each of the first release layer and the second release layer.

6. A package configured to contain and provide for sterile presentation of a product, the package comprising:
    a housing portion defining an interior product storage cavity and comprising a first part of a first film, a first part of a second film, and a first part of a bonding layer coupling the first part of the first film to the first part of the second film;
    a handling portion configured to extend away from the storage cavity of the housing portion, the handling portion comprising a second part of the first film, a second part of the second film, and a second part of the bonding layer coupling the second part of the first film to the second part of the second film; and
a separation feature configured to facilitate separation of the handling portion and the housing portion, the separation feature comprising a first release layer and a second release layer adjacent to the first release layer provided between the first film and the second film at an overlapping portion of the housing portion and the handling portion, wherein the first release layer is made from a first material having a first bond strength and the second release layer is made from a second material having a second bond strength that is greater than the first bond strength.

* * * * *

UNITED STATES PATENT AND TRADEMARK OFFICE
CERTIFICATE OF CORRECTION

PATENT NO. : 10,266,329 B2  
APPLICATION NO. : 15/175908  
DATED : April 23, 2019  
INVENTOR(S) : Aaron R. Bentz Page 1 of 1

It is certified that error appears in the above-identified patent and that said Letters Patent is hereby corrected as shown below:

On the Title Page

Item (56) References Cited, U.S. Patent Documents:
Delete "3,405,563"
And insert -- 3,405,863. --

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*